US009119925B2

(12) United States Patent
Vandine et al.

(10) Patent No.: US 9,119,925 B2
(45) Date of Patent: Sep. 1, 2015

(54) QUICK INITIATION OF RESPIRATORY SUPPORT VIA A VENTILATOR USER INTERFACE

(75) Inventors: Joseph D. Vandine, Manteca, CA (US); Peter R. Doyle, Vista, CA (US); Warren G. Sanborn, Escondido, CA (US)

(73) Assignee: Covidien LP, Mansfield, MA (US)

( * ) Notice: Subject to any disclaimer, the term of this patent is extended or adjusted under 35 U.S.C. 154(b) by 413 days.

(21) Appl. No.: 12/760,649

(22) Filed: Apr. 15, 2010

(65) Prior Publication Data

US 2011/0138315 A1 Jun. 9, 2011

Related U.S. Application Data

(60) Provisional application No. 61/266,953, filed on Dec. 4, 2009.

(51) Int. Cl.

| G06F 3/048 | (2013.01) |
|---|---|
| F16K 31/02 | (2006.01) |
| A61M 16/00 | (2006.01) |
| A61M 16/04 | (2006.01) |

(52) U.S. Cl.
CPC ....... *A61M 16/0051* (2013.01); *A61M 16/0443* (2014.02); *A61M 2205/505* (2013.01)

(58) Field of Classification Search
USPC ...................... 715/780, 781, 810; 128/204.21
See application file for complete search history.

(56) References Cited

U.S. PATENT DOCUMENTS

| 3,577,984 A | 5/1971 | Levy et al. |
|---|---|---|
| 3,659,590 A | 5/1972 | Jones et al. |
| 3,871,371 A | 3/1975 | Weigl |

(Continued)

FOREIGN PATENT DOCUMENTS

| EP | 0414777 | 3/1991 |
|---|---|---|
| EP | 1374938 A1 | 1/2004 |

(Continued)

OTHER PUBLICATIONS

PCT International Search Report, Date of mailing Mar. 3, 2011, Applicant's file reference H-RM-01914 WO, International application No. PCT/US2010/058132, International filed Nov. 26, 2010, Applicant Nellcor Puritan Bennett LLC.

(Continued)

*Primary Examiner* — Stephen Alvesteffer
(74) *Attorney, Agent, or Firm* — Merchant & Gould P.C.

(57) ABSTRACT

This disclosure describes improved systems and methods for efficiently configuring respiratory settings and/or parameters in a ventilatory system. Specifically, the present methods and user interface provide an efficient and consistent means for configuring ventilatory settings for a new patient. Specifically, the ventilator may be preconfigured with appropriate parameter settings based on an institution-specific protocol, a physician-specific protocol, or other suitable protocol or specification. Indeed, the present disclosure provides an institution and/or physician with increased control over routine ventilatory settings by pre-configuring the ventilator with these routine settings. Further, the present disclosure provides increased assurance as to the consistency of the routine ventilatory settings by eliminating repeated data entry by clinicians, decreasing the chances of error.

20 Claims, 4 Drawing Sheets
(3 of 4 Drawing Sheet(s) Filed in Color)

(56) References Cited

U.S. PATENT DOCUMENTS

| | | |
|---|---|---|
| 3,940,742 A | 2/1976 | Hudspeth et al. |
| 3,961,624 A | 6/1976 | Weigl |
| 3,961,627 A | 6/1976 | Ernst et al. |
| 3,977,394 A | 8/1976 | Jones et al. |
| 3,991,304 A | 11/1976 | Hillsman |
| 3,996,928 A | 12/1976 | Marx |
| 4,034,743 A | 7/1977 | Greenwood et al. |
| 4,036,217 A | 7/1977 | Ito et al. |
| 4,053,951 A | 10/1977 | Hudspeth et al. |
| 4,090,513 A | 5/1978 | Togawa |
| 4,112,931 A | 9/1978 | Burns |
| 4,187,842 A | 2/1980 | Schreiber |
| 4,215,409 A | 7/1980 | Strowe |
| 4,241,739 A | 12/1980 | Elson |
| 4,258,718 A | 3/1981 | Goldman |
| 4,296,756 A | 10/1981 | Dunning et al. |
| 4,308,872 A | 1/1982 | Watson et al. |
| 4,323,064 A | 4/1982 | Hoenig et al. |
| 4,326,513 A | 4/1982 | Schulz et al. |
| 4,391,283 A | 7/1983 | Sharpless et al. |
| 4,401,115 A | 8/1983 | Monnier |
| 4,401,116 A | 8/1983 | Fry et al. |
| 4,407,295 A | 10/1983 | Steuer et al. |
| 4,440,177 A | 4/1984 | Anderson et al. |
| 4,444,201 A | 4/1984 | Itoh |
| 4,463,764 A | 8/1984 | Anderson et al. |
| 4,473,081 A | 9/1984 | Dioguardi et al. |
| 4,495,944 A | 1/1985 | Brisson et al. |
| 4,537,190 A | 8/1985 | Caillot et al. |
| 4,550,726 A | 11/1985 | McEwen |
| 4,579,115 A | 4/1986 | Wallroth et al. |
| 4,637,385 A | 1/1987 | Rusz |
| 4,654,029 A | 3/1987 | D'Antonio |
| 4,736,750 A | 4/1988 | Valdespino et al. |
| 4,752,089 A | 6/1988 | Carter |
| 4,790,327 A | 12/1988 | Despotis |
| 4,796,639 A | 1/1989 | Snow et al. |
| 4,813,409 A | 3/1989 | Ismach |
| 4,852,582 A | 8/1989 | Pell |
| 4,867,152 A | 9/1989 | Kou et al. |
| 4,876,903 A | 10/1989 | Budinger |
| 4,878,175 A | 10/1989 | Norden-Paul et al. |
| 4,917,108 A | 4/1990 | Mault |
| 4,921,642 A | 5/1990 | LaTorraca |
| 4,954,799 A | 9/1990 | Kumar |
| 4,984,158 A | 1/1991 | Hillsman |
| 4,990,894 A | 2/1991 | Loescher et al. |
| 5,003,985 A | 4/1991 | White et al. |
| 5,004,472 A | 4/1991 | Wallace |
| 5,009,662 A | 4/1991 | Wallace et al. |
| 5,020,527 A | 6/1991 | Dessertine |
| 5,021,046 A | 6/1991 | Wallace |
| 5,057,822 A | 10/1991 | Hoffman |
| 5,058,601 A | 10/1991 | Riker |
| 5,072,737 A | 12/1991 | Goulding |
| 5,137,026 A | 8/1992 | Waterson et al. |
| 5,150,291 A | 9/1992 | Cummings et al. |
| 5,161,525 A | 11/1992 | Kimm et al. |
| 5,163,423 A | 11/1992 | Suzuki |
| 5,167,506 A | 12/1992 | Kilis et al. |
| 5,203,343 A | 4/1993 | Axe et al. |
| 5,224,487 A | 7/1993 | Bellofatto et al. |
| 5,231,981 A | 8/1993 | Schreiber et al. |
| 5,235,973 A | 8/1993 | Levinson |
| 5,237,987 A | 8/1993 | Anderson et al. |
| 5,246,010 A | 9/1993 | Gazzara et al. |
| 5,251,632 A | 10/1993 | Delpy |
| 5,253,362 A | 10/1993 | Nolan et al. |
| 5,261,397 A | 11/1993 | Grunstein |
| 5,261,415 A | 11/1993 | Dussault |
| 5,271,389 A | 12/1993 | Isaza et al. |
| 5,277,195 A | 1/1994 | Williams |
| 5,279,304 A | 1/1994 | Einhorn et al. |
| 5,279,549 A | 1/1994 | Ranford |
| 5,293,875 A | 3/1994 | Stone |
| 5,299,568 A | 4/1994 | Forare et al. |
| 5,301,921 A | 4/1994 | Kumar |
| 5,303,698 A | 4/1994 | Tobia et al. |
| 5,303,699 A | 4/1994 | Bonassa et al. |
| 5,307,795 A | 5/1994 | Whitwam et al. |
| 5,319,355 A | 6/1994 | Russek |
| 5,319,540 A | 6/1994 | Isaza et al. |
| 5,325,861 A | 7/1994 | Goulding |
| 5,333,106 A | 7/1994 | Lanpher et al. |
| 5,333,606 A | 8/1994 | Schneider et al. |
| 5,339,807 A | 8/1994 | Carter |
| 5,339,825 A | 8/1994 | McNaughton et al. |
| 5,343,857 A | 9/1994 | Schneider et al. |
| 5,351,522 A | 10/1994 | Lura |
| 5,355,893 A | 10/1994 | Mick et al. |
| 5,357,946 A | 10/1994 | Kee et al. |
| 5,357,975 A | 10/1994 | Kraemer et al. |
| 5,363,842 A | 11/1994 | Mishelevich et al. |
| 5,365,922 A | 11/1994 | Raemer |
| 5,368,019 A | 11/1994 | LaTorraca |
| 5,373,851 A | 12/1994 | Reinhold, Jr. et al. |
| 5,377,671 A | 1/1995 | Biondi et al. |
| 5,383,449 A | 1/1995 | Forare et al. |
| 5,383,470 A | 1/1995 | Kolbly |
| 5,385,142 A | 1/1995 | Brady et al. |
| 5,390,666 A | 2/1995 | Kimm et al. |
| 5,401,135 A | 3/1995 | Stoen et al. |
| 5,402,796 A | 4/1995 | Packer et al. |
| 5,404,871 A | 4/1995 | Goodman et al. |
| 5,407,174 A | 4/1995 | Kumar |
| 5,413,110 A | 5/1995 | Cummings et al. |
| 5,438,980 A | 8/1995 | Phillips |
| 5,442,940 A | 8/1995 | Secker et al. |
| 5,443,075 A | 8/1995 | Holscher |
| 5,445,160 A | 8/1995 | Culver et al. |
| 5,446,449 A | 8/1995 | Lhomer et al. |
| 5,448,996 A | 9/1995 | Bellin et al. |
| 5,452,714 A | 9/1995 | Anderson et al. |
| 5,456,264 A | 10/1995 | Series et al. |
| 5,464,410 A | 11/1995 | Skeens et al. |
| 5,479,939 A | 1/1996 | Ogino |
| 5,487,731 A | 1/1996 | Denton |
| 5,495,848 A | 3/1996 | Aylsworth et al. |
| 5,501,231 A | 3/1996 | Kaish |
| 5,507,291 A | 4/1996 | Stirbl et al. |
| 5,513,631 A | 5/1996 | McWilliams |
| 5,517,983 A | 5/1996 | Deighan et al. |
| 5,517,985 A | 5/1996 | Kirk et al. |
| 5,518,002 A | 5/1996 | Wolf et al. |
| 5,520,071 A | 5/1996 | Jones |
| 5,524,615 A | 6/1996 | Power |
| 5,531,221 A | 7/1996 | Power |
| 5,534,851 A | 7/1996 | Russek |
| 5,537,992 A | 7/1996 | Bjoernstijerna et al. |
| 5,542,410 A | 8/1996 | Goodman et al. |
| 5,542,415 A | 8/1996 | Brody |
| 5,544,674 A | 8/1996 | Kelly |
| 5,548,702 A | 8/1996 | Li et al. |
| 5,549,106 A | 8/1996 | Gruenke et al. |
| 5,549,117 A | 8/1996 | Tacklind et al. |
| 5,553,620 A | 9/1996 | Snider |
| 5,558,086 A | 9/1996 | Smith et al. |
| 5,560,353 A | 10/1996 | Willemot et al. |
| 5,564,414 A | 10/1996 | Walker et al. |
| 5,564,432 A | 10/1996 | Thomson |
| 5,571,142 A | 11/1996 | Brown et al. |
| 5,575,283 A | 11/1996 | Sjoestrand |
| 5,582,167 A | 12/1996 | Joseph |
| 5,590,648 A | 1/1997 | Mitchell et al. |
| 5,591,130 A | 1/1997 | Denton |
| 5,596,984 A | 1/1997 | O'Mahony et al. |
| 5,606,976 A | 3/1997 | Marshall |
| 5,611,335 A | 3/1997 | Makhoul et al. |
| 5,626,144 A | 5/1997 | Tacklind et al. |
| 5,630,411 A | 5/1997 | Holscher |
| 5,632,270 A | 5/1997 | O'Mahony et al. |
| 5,632,281 A | 5/1997 | Rayburn |
| 5,634,461 A | 6/1997 | Faithfull et al. |
| 5,634,471 A | 6/1997 | Fairfax et al. |

(56) References Cited

U.S. PATENT DOCUMENTS

| | | | |
|---|---|---|---|
| 5,642,735 | A | 7/1997 | Kolbly |
| 5,645,048 | A | 7/1997 | Brodsky et al. |
| 5,647,346 | A | 7/1997 | Holscher |
| 5,651,264 | A | 7/1997 | Lo et al. |
| 5,655,516 | A | 8/1997 | Goodman et al. |
| 5,660,168 | A | 8/1997 | Ottosson et al. |
| 5,660,171 | A | 8/1997 | Kimm et al. |
| 5,664,560 | A | 9/1997 | Merrick et al. |
| 5,664,562 | A | 9/1997 | Bourdon |
| 5,669,379 | A | 9/1997 | Somerson et al. |
| 5,671,767 | A | 9/1997 | Kelly |
| 5,672,041 | A | 9/1997 | Ringdahl et al. |
| 5,673,689 | A | 10/1997 | Power |
| 5,676,129 | A | 10/1997 | Rocci, Jr. et al. |
| 5,676,132 | A | 10/1997 | Tillotson et al. |
| 5,678,539 | A | 10/1997 | Schubert et al. |
| 5,683,424 | A | 11/1997 | Brown et al. |
| 5,692,497 | A | 12/1997 | Schnitzer et al. |
| 5,697,959 | A | 12/1997 | Poore |
| 5,704,346 | A | 1/1998 | Inoue |
| 5,704,366 | A | 1/1998 | Tacklind et al. |
| 5,704,367 | A | 1/1998 | Ishikawa et al. |
| 5,706,801 | A | 1/1998 | Remes et al. |
| 5,715,812 | A | 2/1998 | Deighan et al. |
| 5,724,990 | A | 3/1998 | Ogino |
| 5,730,140 | A | 3/1998 | Fitch |
| 5,730,145 | A | 3/1998 | Defares et al. |
| 5,735,287 | A | 4/1998 | Thomson |
| 5,736,974 | A | 4/1998 | Selker |
| 5,738,092 | A | 4/1998 | Mock et al. |
| 5,740,792 | A | 4/1998 | Ashley et al. |
| 5,743,267 | A | 4/1998 | Nikolic et al. |
| 5,752,506 | A | 5/1998 | Richardson |
| 5,752,509 | A | 5/1998 | Lachmann et al. |
| 5,755,218 | A | 5/1998 | Johansson et al. |
| 5,758,652 | A | 6/1998 | Nikolic |
| 5,762,480 | A | 6/1998 | Adahan |
| 5,769,082 | A * | 6/1998 | Perel ........................ 600/484 |
| 5,771,884 | A | 6/1998 | Yarnall et al. |
| 5,778,874 | A | 7/1998 | Maguire et al. |
| 5,791,339 | A | 8/1998 | Winter |
| 5,794,612 | A | 8/1998 | Wachter et al. |
| 5,794,986 | A | 8/1998 | Gansel et al. |
| 5,800,361 | A | 9/1998 | Rayburn |
| 5,806,514 | A | 9/1998 | Mock et al. |
| 5,809,997 | A | 9/1998 | Wolf |
| 5,813,397 | A | 9/1998 | Goodman et al. |
| 5,813,399 | A | 9/1998 | Isaza et al. |
| 5,819,723 | A | 10/1998 | Joseph |
| 5,822,715 | A | 10/1998 | Worthington et al. |
| 5,826,570 | A | 10/1998 | Goodman et al. |
| 5,826,575 | A | 10/1998 | Lall |
| 5,827,179 | A | 10/1998 | Lichter et al. |
| 5,829,441 | A | 11/1998 | Kidd et al. |
| 5,839,430 | A | 11/1998 | Cama |
| 5,864,938 | A | 2/1999 | Gansel et al. |
| 5,865,168 | A | 2/1999 | Isaza |
| 5,865,171 | A | 2/1999 | Cinquin |
| 5,865,174 | A | 2/1999 | Kloeppel |
| 5,875,777 | A | 3/1999 | Eriksson |
| 5,878,744 | A | 3/1999 | Pfeiffer |
| 5,881,717 | A | 3/1999 | Isaza |
| 5,881,723 | A | 3/1999 | Wallace |
| 5,884,622 | A | 3/1999 | Younes |
| 5,884,623 | A | 3/1999 | Winter |
| 5,891,023 | A | 4/1999 | Lynn |
| 5,899,203 | A | 5/1999 | Defares et al. |
| 5,909,731 | A | 6/1999 | O'Mahony et al. |
| 5,915,379 | A | 6/1999 | Wallace |
| 5,915,380 | A | 6/1999 | Wallace |
| 5,915,382 | A | 6/1999 | Power |
| 5,918,597 | A | 7/1999 | Jones et al. |
| 5,921,238 | A | 7/1999 | Bourdon |
| 5,921,920 | A | 7/1999 | Marshall et al. |
| 5,924,418 | A | 7/1999 | Lewis |
| 5,931,160 | A | 8/1999 | Gilmore |
| 5,932,812 | A | 8/1999 | Delsing |
| 5,934,274 | A | 8/1999 | Merrick et al. |
| 5,937,854 | A | 8/1999 | Stenzler |
| 5,956,501 | A | 9/1999 | Brown |
| 5,957,861 | A | 9/1999 | Combs et al. |
| 5,971,937 | A | 10/1999 | Ekstrom |
| 5,975,081 | A | 11/1999 | Hood |
| 5,979,440 | A | 11/1999 | Honkonen et al. |
| 5,980,466 | A | 11/1999 | Thomson |
| 6,012,450 | A | 1/2000 | Rubsamen |
| 6,017,315 | A | 1/2000 | Starr |
| 6,024,089 | A | 2/2000 | Wallace |
| 6,026,323 | A | 2/2000 | Skladnev et al. |
| 6,032,119 | A | 2/2000 | Brown et al. |
| 6,041,780 | A | 3/2000 | Richard et al. |
| 6,047,860 | A | 4/2000 | Sanders |
| 6,055,506 | A | 4/2000 | Frasca, Jr. |
| 6,073,110 | A | 6/2000 | Rhodes et al. |
| 6,076,523 | A | 6/2000 | Jones et al. |
| 6,099,481 | A | 8/2000 | Daniels et al. |
| 6,106,481 | A | 8/2000 | Cohen |
| 6,116,240 | A | 9/2000 | Merrick et al. |
| 6,116,464 | A | 9/2000 | Sanders |
| 6,118,847 | A | 9/2000 | Hernandez-Guerra |
| 6,119,684 | A | 9/2000 | Nohl et al. |
| 6,123,073 | A | 9/2000 | Schlawin et al. |
| 6,135,106 | A | 10/2000 | Dirks et al. |
| 6,142,150 | A | 11/2000 | O'Mahoney et al. |
| 6,148,814 | A * | 11/2000 | Clemmer et al. ........ 128/200.24 |
| 6,148,815 | A | 11/2000 | Wolf |
| 6,155,257 | A | 12/2000 | Lurie et al. |
| 6,158,432 | A | 12/2000 | Biondi |
| 6,159,147 | A | 12/2000 | Lichter et al. |
| 6,161,539 | A | 12/2000 | Winter |
| 6,162,183 | A | 12/2000 | Hoover |
| 6,167,362 | A | 12/2000 | Brown et al. |
| 6,167,412 | A | 12/2000 | Simons |
| 6,168,568 | B1 | 1/2001 | Gavriely |
| 6,171,264 | B1 | 1/2001 | Bader |
| 6,176,833 | B1 | 1/2001 | Thomson |
| 6,186,956 | B1 | 2/2001 | McNamee |
| 6,190,326 | B1 | 2/2001 | McKinnon et al. |
| 6,192,876 | B1 | 2/2001 | Denyer et al. |
| 6,198,963 | B1 | 3/2001 | Haim et al. |
| 6,199,550 | B1 | 3/2001 | Wiesmann et al. |
| 6,202,642 | B1 | 3/2001 | McKinnon et al. |
| 6,213,955 | B1 | 4/2001 | Karakasoglu et al. |
| 6,220,245 | B1 | 4/2001 | Takabayashi et al. |
| 6,223,744 | B1 | 5/2001 | Garon |
| 6,224,553 | B1 | 5/2001 | Nevo |
| 6,233,539 | B1 | 5/2001 | Brown |
| 6,234,963 | B1 | 5/2001 | Blike et al. |
| 6,240,920 | B1 | 6/2001 | Strom |
| 6,240,921 | B1 | 6/2001 | Brydon et al. |
| 6,251,082 | B1 | 6/2001 | Rayburn |
| 6,261,238 | B1 | 7/2001 | Gavriely |
| 6,262,728 | B1 | 7/2001 | Alexander |
| 6,269,810 | B1 | 8/2001 | Brooker et al. |
| 6,269,812 | B1 | 8/2001 | Wallace |
| 6,273,088 | B1 | 8/2001 | Hillsman |
| 6,273,444 | B1 | 8/2001 | Power |
| 6,279,574 | B1 | 8/2001 | Richardson et al. |
| 6,283,119 | B1 | 9/2001 | Bourdon |
| 6,283,923 | B1 | 9/2001 | Finkelstein et al. |
| 6,287,264 | B1 | 9/2001 | Hoffman |
| 6,301,497 | B1 | 10/2001 | Neustadter |
| 6,302,106 | B1 | 10/2001 | Lewis |
| 6,305,373 | B1 | 10/2001 | Wallace |
| 6,321,748 | B1 | 11/2001 | O'Mahoney |
| 6,322,502 | B1 | 11/2001 | Schoenberg et al. |
| 6,325,785 | B1 | 12/2001 | Babkes et al. |
| 6,339,410 | B1 | 1/2002 | Milner |
| 6,340,348 | B1 | 1/2002 | Krishnan |
| 6,342,040 | B1 | 1/2002 | Starr |
| 6,349,722 | B1 | 2/2002 | Gradon et al. |
| 6,349,724 | B1 | 2/2002 | Burton et al. |
| 6,355,002 | B1 | 3/2002 | Faram et al. |
| 6,357,438 | B1 | 3/2002 | Hansen |

(56) References Cited

U.S. PATENT DOCUMENTS

| | | | |
|---|---|---|---|
| 6,360,745 B1 | 3/2002 | Wallace |
| 6,362,620 B1 | 3/2002 | Debbins |
| 6,367,475 B1 | 4/2002 | Kofoed et al. |
| 6,369,838 B1 | 4/2002 | Wallace |
| 6,370,419 B1 | 4/2002 | Lampotang |
| 6,377,046 B1 | 4/2002 | Debbins |
| 6,379,301 B1 | 4/2002 | Worthington et al. |
| 6,390,088 B1 | 5/2002 | Nohl et al. |
| 6,390,091 B1 | 5/2002 | Banner et al. |
| 6,390,092 B1 | 5/2002 | Leenhoven |
| 6,390,977 B1 | 5/2002 | Faithfull et al. |
| 6,402,698 B1 | 6/2002 | Mault |
| 6,408,043 B1 | 6/2002 | Hu |
| 6,412,483 B1 | 7/2002 | Jones et al. |
| 6,415,792 B1 | 7/2002 | Schoolman |
| 6,416,471 B1 | 7/2002 | Kumar et al. |
| 6,421,650 B1 | 7/2002 | Goetz et al. |
| 6,427,687 B1 | 8/2002 | Kirk |
| 6,435,175 B1 | 8/2002 | Stenzler |
| 6,436,053 B1 | 8/2002 | Knapp, II et al. |
| 6,439,229 B1 | 8/2002 | Du et al. |
| 6,450,164 B1 | 9/2002 | Banner et al. |
| 6,454,708 B1 | 9/2002 | Ferguson et al. |
| 6,459,933 B1 | 10/2002 | Lurie et al. |
| 6,463,930 B2 | 10/2002 | Biondi et al. |
| 6,467,478 B1 | 10/2002 | Merrick et al. |
| 6,471,658 B1 | 10/2002 | Daniels et al. |
| 6,488,029 B1 | 12/2002 | Hood |
| 6,488,629 B1 | 12/2002 | Saetre |
| RE37,970 E | 1/2003 | Costello, Jr. |
| 6,511,426 B1 | 1/2003 | Hossack |
| 6,512,938 B2 | 1/2003 | Claure |
| 6,515,683 B1 | 2/2003 | Wright |
| 6,517,497 B2 | 2/2003 | Rymut et al. |
| 6,533,723 B1 | 3/2003 | Lockery |
| 6,533,730 B2 | 3/2003 | Strom |
| 6,543,449 B1 | 4/2003 | Woodring |
| 6,543,701 B1 | 4/2003 | Ho |
| 6,544,192 B2 | 4/2003 | Starr |
| 6,546,930 B1 | 4/2003 | Emerson et al. |
| 6,547,728 B1 | 4/2003 | Cornuejols |
| 6,553,991 B1 | 4/2003 | Isaza |
| 6,553,992 B1 | 4/2003 | Berthon-Jones et al. |
| 6,557,553 B1 | 5/2003 | Borrello |
| 6,557,554 B1 | 5/2003 | Sugiura |
| 6,566,875 B1 | 5/2003 | Hasson |
| 6,571,122 B2 | 5/2003 | Schroeppel et al. |
| 6,571,795 B2 | 6/2003 | Bourdon |
| 6,571,796 B2 | 6/2003 | Banner et al. |
| 6,578,575 B1 | 6/2003 | Jonson |
| 6,581,592 B1 | 6/2003 | Bathe et al. |
| 6,584,973 B1 | 7/2003 | Biondi |
| 6,597,939 B1 | 7/2003 | Lampotang |
| 6,599,252 B2 | 7/2003 | Starr |
| 6,603,494 B1 | 8/2003 | Banks |
| 6,606,993 B1 | 8/2003 | Wiesmann et al. |
| 6,609,016 B1 | 8/2003 | Lynn |
| 6,620,106 B2 | 9/2003 | Mault |
| 6,621,917 B1 | 9/2003 | Vilser |
| 6,622,726 B1 | 9/2003 | Du |
| 6,629,934 B2 | 10/2003 | Mault et al. |
| 6,630,176 B2 | 10/2003 | Li |
| 6,644,310 B1 | 11/2003 | Delache et al. |
| 6,644,312 B2 | 11/2003 | Berthon-Jones et al. |
| 6,645,158 B2 | 11/2003 | Mault |
| 6,650,346 B1 | 11/2003 | Jaeger |
| 6,651,653 B1 | 11/2003 | Honkonen et al. |
| 6,656,129 B2 | 12/2003 | Niles et al. |
| 6,668,824 B1 | 12/2003 | Isaza et al. |
| 6,668,829 B2 | 12/2003 | Biondi |
| 6,671,529 B2 | 12/2003 | Claure |
| 6,673,018 B2 | 1/2004 | Friedman |
| 6,675,801 B2 | 1/2004 | Wallace |
| 6,679,258 B1 | 1/2004 | Strom |
| 6,681,764 B1 | 1/2004 | Honkonen et al. |
| 6,698,423 B1 | 3/2004 | Honkonen et al. |
| 6,707,476 B1 | 3/2004 | Hochstedler |
| 6,708,688 B1 | 3/2004 | Rubin et al. |
| 6,709,405 B2 | 3/2004 | Jonson |
| 6,712,762 B1 | 3/2004 | Lichter et al. |
| 6,718,974 B1 | 4/2004 | Moberg |
| 6,718,975 B1 | 4/2004 | Blomberg |
| 6,725,077 B1 | 4/2004 | Balloni |
| 6,725,447 B1 | 4/2004 | Gilman et al. |
| 6,725,860 B2 | 4/2004 | Wallroth et al. |
| 6,733,449 B1 | 5/2004 | Krishnamurthy |
| 6,738,079 B1 | 5/2004 | Kellerman et al. |
| 6,739,337 B2 | 5/2004 | Isaza |
| 6,740,046 B2 | 5/2004 | Knapp, II et al. |
| 6,743,172 B1 | 6/2004 | Blike |
| 6,744,374 B1 | 6/2004 | Kuenzner |
| 6,745,764 B2 | 6/2004 | Hickle |
| 6,755,193 B2 | 6/2004 | Berthon-Jones et al. |
| 6,755,787 B2 | 6/2004 | Hossack |
| 6,760,610 B2 | 7/2004 | Tschupp et al. |
| 6,761,167 B1 | 7/2004 | Nadjafizadeh et al. |
| 6,761,168 B1 | 7/2004 | Nadjafizadeh et al. |
| 6,776,159 B2 | 8/2004 | Pelerossi et al. |
| 6,782,888 B1 | 8/2004 | Friberg |
| 6,790,178 B1 | 9/2004 | Mault et al. |
| 6,792,066 B1 | 9/2004 | Harder |
| 6,796,305 B1 | 9/2004 | Banner et al. |
| 6,801,227 B2 | 10/2004 | Bocionek |
| 6,801,802 B2 | 10/2004 | Sitzman et al. |
| 6,805,118 B2 | 10/2004 | Brooker et al. |
| 6,807,965 B1 | 10/2004 | Hickle |
| 6,814,074 B1 | 11/2004 | Nadjafizadeh et al. |
| 6,820,614 B2 | 11/2004 | Bonutti |
| 6,820,618 B2 | 11/2004 | Banner et al. |
| 6,822,223 B2 | 11/2004 | Davis |
| 6,824,520 B2 | 11/2004 | Orr et al. |
| 6,828,910 B2 | 12/2004 | VanRyzin et al. |
| 6,830,046 B2 | 12/2004 | Blakley et al. |
| 6,834,647 B2 | 12/2004 | Blair et al. |
| 6,837,242 B2 | 1/2005 | Younes |
| 6,839,753 B2 | 1/2005 | Biondi |
| 6,845,773 B2 | 1/2005 | Berthon-Jones et al. |
| 6,858,006 B2 | 2/2005 | MacCarter et al. |
| 6,860,266 B2 | 3/2005 | Blike |
| 6,866,040 B1 | 3/2005 | Bourdon |
| 6,866,629 B2 | 3/2005 | Bardy |
| 6,893,397 B2 | 5/2005 | Bardy |
| 6,899,103 B1 | 5/2005 | Hood |
| 6,899,683 B2 | 5/2005 | Mault et al. |
| 6,899,684 B2 | 5/2005 | Mault et al. |
| 6,910,480 B1 | 6/2005 | Berthon-Jones |
| 6,910,481 B2 | 6/2005 | Kimmel et al. |
| 6,921,369 B1 | 7/2005 | Gehrke et al. |
| 6,923,079 B1 | 8/2005 | Snibbe |
| 6,931,269 B2 | 8/2005 | Terry |
| 6,932,083 B2 | 8/2005 | Jones et al. |
| 6,932,767 B2 | 8/2005 | Landry |
| 6,932,774 B2 | 8/2005 | Nakatani et al. |
| 6,947,780 B2 | 9/2005 | Scharf |
| 6,951,541 B2 | 10/2005 | Desmarais |
| 6,954,702 B2 | 10/2005 | Pierry et al. |
| 6,956,572 B2 | 10/2005 | Zaleski |
| 6,960,854 B2 | 11/2005 | Nadjafizadeh et al. |
| 6,970,919 B1 | 11/2005 | Doi |
| 6,976,487 B1 | 12/2005 | Melker et al. |
| 6,976,958 B2 | 12/2005 | Quy |
| 6,986,347 B2 | 1/2006 | Hickle |
| 6,997,185 B2 | 2/2006 | Han et al. |
| 6,997,880 B2 | 2/2006 | Carlebach et al. |
| 6,997,881 B2 | 2/2006 | Green et al. |
| 7,006,862 B2 | 2/2006 | Kaufman et al. |
| 7,008,380 B1 | 3/2006 | Rees et al. |
| 7,017,574 B2 | 3/2006 | Biondi |
| 7,019,652 B2 | 3/2006 | Richardson |
| 7,033,323 B2 | 4/2006 | Botbol et al. |
| 7,036,504 B2 | 5/2006 | Wallace |
| 7,039,878 B2 | 5/2006 | Auer |
| 7,040,315 B1 | 5/2006 | Strömberg |
| 7,040,318 B2 | 5/2006 | Däscher et al. |

(56) References Cited

U.S. PATENT DOCUMENTS

| | | |
|---|---|---|
| 7,040,321 B2 | 5/2006 | Göbel |
| 7,046,254 B2 | 5/2006 | Brown et al. |
| 7,047,092 B2 | 5/2006 | Wimsatt |
| 7,051,736 B2 | 5/2006 | Banner et al. |
| 7,055,522 B2 | 6/2006 | Berthon Jones |
| 7,062,251 B2 | 6/2006 | Birkett |
| 7,066,173 B2 | 6/2006 | Banner et al. |
| 7,077,125 B2 | 7/2006 | Scheuch |
| 7,077,131 B2 | 7/2006 | Hansen |
| 7,081,091 B2 | 7/2006 | Merrett et al. |
| 7,081,095 B2 | 7/2006 | Lynn |
| RE39,225 E | 8/2006 | Isaza et al. |
| 7,083,574 B2 | 8/2006 | Kline |
| 7,089,927 B2 | 8/2006 | John et al. |
| 7,089,937 B2 | 8/2006 | Berthon-Jones et al. |
| 7,094,208 B2 | 8/2006 | Williams et al. |
| 7,116,810 B2 | 10/2006 | Miller et al. |
| 7,117,438 B2 | 10/2006 | Wallace |
| 7,128,578 B2 | 10/2006 | Lampotang |
| 7,137,074 B1 | 11/2006 | Newton et al. |
| 7,147,600 B2 | 12/2006 | Bardy |
| 7,156,808 B2 | 1/2007 | Quy |
| 7,162,296 B2 | 1/2007 | Leonhardt et al. |
| 7,164,972 B2 | 1/2007 | Imhof et al. |
| 7,165,221 B2 | 1/2007 | Monteleone |
| 7,169,112 B2 | 1/2007 | Caldwell |
| 7,172,557 B1 | 2/2007 | Parker |
| 7,182,083 B2 | 2/2007 | Yanof et al. |
| 7,187,790 B2 | 3/2007 | Sabol |
| 7,188,621 B2 | 3/2007 | DeVries |
| 7,201,734 B2 | 4/2007 | Hickle |
| 7,203,353 B2 | 4/2007 | Klotz |
| 7,207,945 B2 | 4/2007 | Bardy |
| 7,210,478 B2 | 5/2007 | Banner et al. |
| 7,211,049 B2 | 5/2007 | Bradley et al. |
| 7,219,666 B2 | 5/2007 | Friberg et al. |
| 7,220,230 B2 | 5/2007 | Roteliuk et al. |
| 7,222,054 B2 | 5/2007 | Geva |
| 7,223,965 B2 | 5/2007 | Davis |
| 7,228,323 B2 | 6/2007 | Angerer et al. |
| 7,241,269 B2 | 7/2007 | McCawley et al. |
| 7,246,618 B2 | 7/2007 | Habashi |
| 7,247,154 B2 | 7/2007 | Hickle |
| 7,252,640 B2 | 8/2007 | Ni et al. |
| 7,261,690 B2 | 8/2007 | Teller et al. |
| 7,264,730 B2 | 9/2007 | Connell |
| 7,270,126 B2 | 9/2007 | Wallace |
| 7,275,540 B2 | 10/2007 | Bolam et al. |
| 7,278,579 B2 | 10/2007 | Loffredo |
| 7,282,032 B2 | 10/2007 | Miller |
| 7,285,090 B2 | 10/2007 | Stivoric et al. |
| 7,294,105 B1 | 11/2007 | Islam |
| 7,294,112 B1 | 11/2007 | Dunlop |
| 7,298,280 B2 | 11/2007 | Voege et al. |
| 7,300,418 B2 | 11/2007 | Zaleski |
| 7,303,680 B2 | 12/2007 | Connell |
| 7,308,550 B2 | 12/2007 | Cornett |
| 7,310,551 B1 | 12/2007 | Koh et al. |
| 7,310,720 B2 | 12/2007 | Cornett |
| 7,311,665 B2 | 12/2007 | Hawthorne et al. |
| 7,314,451 B2 | 1/2008 | Halperin et al. |
| 7,316,231 B2 | 1/2008 | Hickle |
| 7,318,808 B2 | 1/2008 | Tarassenko et al. |
| 7,318,892 B2 | 1/2008 | Connell |
| 7,321,802 B2 | 1/2008 | Wasner et al. |
| 7,322,352 B2 | 1/2008 | Minshull et al. |
| 7,322,937 B2 | 1/2008 | Blomberg et al. |
| 7,331,340 B2 | 2/2008 | Barney |
| 7,333,969 B2 | 2/2008 | Lee |
| 7,334,578 B2 | 2/2008 | Biondi |
| 7,343,916 B2 | 3/2008 | Biondo et al. |
| 7,343,917 B2 | 3/2008 | Jones |
| 7,347,200 B2 | 3/2008 | Jones et al. |
| 7,347,207 B2 | 3/2008 | Ahlmen et al. |
| 7,351,340 B2 | 4/2008 | Connell |
| 7,362,341 B2 | 4/2008 | McGuire et al. |
| 7,366,572 B2 | 4/2008 | Heruth et al. |
| 7,367,337 B2 | 5/2008 | Berthon-Jones et al. |
| 7,367,955 B2 | 5/2008 | Zhang et al. |
| 7,369,757 B2 | 5/2008 | Farbarik |
| 7,370,650 B2 | 5/2008 | Nadjafizadeh et al. |
| 7,374,535 B2 | 5/2008 | Schoenberg et al. |
| 7,377,276 B2 | 5/2008 | Roy |
| 7,380,210 B2 | 5/2008 | Lontka et al. |
| RE40,365 E | 6/2008 | Kirchgeorg et al. |
| 7,383,148 B2 | 6/2008 | Ahmed |
| 7,387,610 B2 | 6/2008 | Stahmann et al. |
| 7,413,546 B2 | 8/2008 | Agutter et al. |
| 7,422,562 B2 | 9/2008 | Hatib et al. |
| 7,425,201 B2 | 9/2008 | Euliano et al. |
| 7,428,902 B2 | 9/2008 | Du et al. |
| 7,435,220 B2 | 10/2008 | Ranucci |
| 7,438,072 B2 | 10/2008 | Izuchukwu |
| 7,438,073 B2 | 10/2008 | Delache et al. |
| 7,448,383 B2 | 11/2008 | Delache et al. |
| 7,452,333 B2 | 11/2008 | Roteliuk |
| 7,460,959 B2 | 12/2008 | Jafari |
| 7,464,339 B2 | 12/2008 | Keenan, Jr. et al. |
| 7,469,698 B1 | 12/2008 | Childers et al. |
| 7,487,773 B2 | 2/2009 | Li |
| 7,487,774 B2 | 2/2009 | Acker |
| 7,490,085 B2 | 2/2009 | Walker |
| 7,496,400 B2 | 2/2009 | Hoskonen et al. |
| 7,500,481 B2 | 3/2009 | Delache et al. |
| 7,504,954 B2 | 3/2009 | Spaeder |
| 7,512,450 B2 | 3/2009 | Ahmed |
| 7,512,593 B2 | 3/2009 | Karklins et al. |
| 7,527,053 B2 | 5/2009 | DeVries et al. |
| 7,527,054 B2 | 5/2009 | Misholi |
| 7,530,353 B2 | 5/2009 | Choncholas et al. |
| RE40,806 E | 6/2009 | Gradon et al. |
| 7,543,582 B2 | 6/2009 | Lu et al. |
| 7,548,833 B2 | 6/2009 | Ahmed |
| 7,552,731 B2 | 6/2009 | Jorczak et al. |
| 7,556,036 B2 | 7/2009 | Bouillon et al. |
| 7,559,903 B2 | 7/2009 | Moussavi et al. |
| 7,562,657 B2 | 7/2009 | Blanch et al. |
| 7,565,905 B2 | 7/2009 | Hickle |
| 7,584,712 B2 | 9/2009 | Lu |
| 7,590,551 B2 | 9/2009 | Auer |
| 7,597,099 B2 | 10/2009 | Jones et al. |
| 7,603,170 B2 | 10/2009 | Hatlestad et al. |
| 7,603,631 B2 | 10/2009 | Bermudez et al. |
| 7,606,668 B2 | 10/2009 | Pierry et al. |
| 7,609,138 B2 | 10/2009 | Dietrich et al. |
| 7,610,915 B2 | 11/2009 | Dittmann |
| 7,618,378 B2 | 11/2009 | Bingham et al. |
| 7,625,345 B2 | 12/2009 | Quinn |
| 7,630,755 B2 | 12/2009 | Stahmann et al. |
| 7,650,181 B2 | 1/2010 | Freeman et al. |
| 7,652,571 B2 | 1/2010 | Parkulo et al. |
| 7,654,802 B2 | 2/2010 | Crawford, Jr. et al. |
| 7,654,966 B2 | 2/2010 | Westinskow et al. |
| 7,658,188 B2 | 2/2010 | Halpern et al. |
| 7,662,106 B2 | 2/2010 | Daniels et al. |
| 7,668,579 B2 | 2/2010 | Lynn |
| 7,669,598 B2 | 3/2010 | Rick et al. |
| 7,671,733 B2 | 3/2010 | McNeal et al. |
| 7,678,063 B2 | 3/2010 | Felmlee et al. |
| 7,682,312 B2 | 3/2010 | Lurie |
| 7,684,931 B2 | 3/2010 | Pierry et al. |
| 7,693,697 B2 | 4/2010 | Westenskow et al. |
| 7,694,677 B2 | 4/2010 | Tang |
| 7,698,156 B2 | 4/2010 | Martucci et al. |
| 7,708,015 B2 | 5/2010 | Seeger et al. |
| 7,717,112 B2 | 5/2010 | Sun et al. |
| 7,717,113 B2 | 5/2010 | Andrieux |
| D618,356 S | 6/2010 | Ross |
| 7,727,160 B2 | 6/2010 | Green et al. |
| 7,731,663 B2 | 6/2010 | Averina et al. |
| 7,736,132 B2 | 6/2010 | Bliss et al. |
| 7,740,013 B2 | 6/2010 | Ishizaki et al. |
| 7,753,049 B2 | 7/2010 | Jorczak et al. |
| 7,766,012 B2 | 8/2010 | Scheuch et al. |

(56) References Cited

U.S. PATENT DOCUMENTS

| | | |
|---|---|---|
| 7,771,364 B2 | 8/2010 | Arbel et al. |
| 7,772,965 B2 | 8/2010 | Farhan et al. |
| 7,778,709 B2 | 8/2010 | Gollasch et al. |
| 7,778,851 B2 | 8/2010 | Schoenberg et al. |
| 7,784,461 B2 | 8/2010 | Figueiredo et al. |
| 7,785,263 B2 | 8/2010 | Roteliuk et al. |
| 7,785,265 B2 | 8/2010 | Schätzl |
| 7,793,659 B2 | 9/2010 | Breen |
| 7,793,660 B2 | 9/2010 | Kimmel et al. |
| 7,810,497 B2 | 10/2010 | Pittman et al. |
| 7,814,906 B2 | 10/2010 | Moretti |
| 7,819,815 B2 | 10/2010 | Younes |
| 7,823,588 B2 | 11/2010 | Hansen |
| 7,831,450 B2 | 11/2010 | Schoenberg et al. |
| 7,832,394 B2 | 11/2010 | Schechter et al. |
| 7,836,882 B1 | 11/2010 | Rumph et al. |
| 7,837,629 B2 | 11/2010 | Bardy |
| 7,850,619 B2 | 12/2010 | Gavish et al. |
| 7,855,656 B2 | 12/2010 | Maschke |
| 7,855,716 B2 | 12/2010 | McCreary et al. |
| 7,859,401 B2 | 12/2010 | Falck et al. |
| 7,866,317 B2 | 1/2011 | Muellinger et al. |
| 7,871,394 B2 | 1/2011 | Halbert et al. |
| D632,796 S | 2/2011 | Ross et al. |
| D632,797 S | 2/2011 | Ross et al. |
| 7,881,780 B2 | 2/2011 | Flaherty |
| 7,883,480 B2 | 2/2011 | Dunlop |
| 7,885,828 B2 | 2/2011 | Glaser-Seidnitzer et al. |
| 7,886,231 B2 | 2/2011 | Hopermann et al. |
| 7,891,353 B2 | 2/2011 | Chalvignac |
| 7,891,354 B2 | 2/2011 | Farbarik |
| 7,893,560 B2 | 2/2011 | Carter |
| 7,895,527 B2 | 2/2011 | Zaleski et al. |
| 7,909,033 B2 | 3/2011 | Faram |
| 7,912,537 B2 | 3/2011 | Lee et al. |
| 7,927,286 B2 | 4/2011 | Ranucci |
| 7,931,601 B2 | 4/2011 | Ranucci |
| D638,852 S | 5/2011 | Skidmore et al. |
| 7,953,419 B2 | 5/2011 | Jost et al. |
| 7,956,719 B2 | 6/2011 | Anderson, Jr. et al. |
| 7,958,892 B2 | 6/2011 | Kwok et al. |
| 7,970,450 B2 | 6/2011 | Kroecker et al. |
| 7,984,714 B2 | 7/2011 | Hausmann et al. |
| D643,535 S | 8/2011 | Ross et al. |
| 7,990,251 B1 * | 8/2011 | Ford, Jr. .................. 340/286.07 |
| 7,992,557 B2 | 8/2011 | Nadjafizadeh et al. |
| 8,001,967 B2 | 8/2011 | Wallace et al. |
| D645,158 S | 9/2011 | Sanchez et al. |
| 8,021,310 B2 | 9/2011 | Sanborn et al. |
| D649,157 S | 11/2011 | Skidmore et al. |
| D653,749 S | 2/2012 | Winter et al. |
| 8,113,062 B2 | 2/2012 | Graboi et al. |
| D655,405 S | 3/2012 | Winter et al. |
| D655,809 S | 3/2012 | Winter et al. |
| 8,181,648 B2 | 5/2012 | Perine et al. |
| 8,210,173 B2 | 7/2012 | Vandine |
| 8,210,174 B2 | 7/2012 | Farbarik |
| 8,239,780 B2 | 8/2012 | Manetta et al. |
| 8,240,684 B2 | 8/2012 | Ross et al. |
| 8,267,085 B2 | 9/2012 | Jafari et al. |
| 8,272,379 B2 | 9/2012 | Jafari et al. |
| 8,272,380 B2 | 9/2012 | Jafari et al. |
| 8,302,600 B2 | 11/2012 | Andrieux et al. |
| 8,302,602 B2 | 11/2012 | Andrieux et al. |
| 8,457,706 B2 | 6/2013 | Baker, Jr. |
| 8,792,949 B2 | 7/2014 | Baker, Jr. |
| 2001/0056358 A1 | 12/2001 | Dulong |
| 2002/0026941 A1 | 3/2002 | Biondi et al. |
| 2002/0044059 A1 | 4/2002 | Reeder |
| 2002/0077863 A1 | 6/2002 | Rutledge |
| 2002/0091548 A1 | 7/2002 | Auer |
| 2002/0171682 A1 | 11/2002 | Frank et al. |
| 2002/0177758 A1 | 11/2002 | Schoenberg et al. |
| 2003/0060723 A1 | 3/2003 | Joo et al. |
| 2003/0062045 A1 | 4/2003 | Woodring |
| 2003/0106553 A1 | 6/2003 | Vanderveen |
| 2003/0130567 A1 | 7/2003 | Mault et al. |
| 2003/0130595 A1 | 7/2003 | Mault |
| 2003/0140928 A1 | 7/2003 | Bui et al. |
| 2003/0140929 A1 | 7/2003 | Wilkes et al. |
| 2003/0141368 A1 | 7/2003 | Pascual et al. |
| 2003/0141981 A1 | 7/2003 | Bui et al. |
| 2003/0142138 A1 | 7/2003 | Brown et al. |
| 2003/0144878 A1 | 7/2003 | Wilkes et al. |
| 2003/0144880 A1 | 7/2003 | Talachian et al. |
| 2003/0144881 A1 | 7/2003 | Talachian et al. |
| 2003/0144882 A1 | 7/2003 | Talachian et al. |
| 2003/0201697 A1 | 10/2003 | Richardson |
| 2003/0204414 A1 | 10/2003 | Wilkes et al. |
| 2003/0204416 A1 | 10/2003 | Radpay et al. |
| 2003/0204419 A1 | 10/2003 | Wilkes et al. |
| 2003/0204420 A1 | 10/2003 | Wilkes et al. |
| 2003/0208152 A1 | 11/2003 | Avrahami et al. |
| 2003/0208465 A1 | 11/2003 | Yurko |
| 2003/0222548 A1 | 12/2003 | Richardson et al. |
| 2003/0230308 A1 | 12/2003 | Linden |
| 2004/0010425 A1 | 1/2004 | Wilkes et al. |
| 2004/0021693 A1 * | 2/2004 | Monteleone .................. 345/781 |
| 2004/0034289 A1 | 2/2004 | Teller et al. |
| 2004/0059604 A1 | 3/2004 | Zaleski |
| 2004/0073453 A1 | 4/2004 | Nenov |
| 2004/0078231 A1 | 4/2004 | Wilkes et al. |
| 2004/0121767 A1 | 6/2004 | Simpson et al. |
| 2004/0122294 A1 | 6/2004 | Hatlestad et al. |
| 2004/0150525 A1 | 8/2004 | Wilson |
| 2004/0167465 A1 | 8/2004 | Mihai et al. |
| 2004/0167804 A1 | 8/2004 | Simpson et al. |
| 2004/0172222 A1 | 9/2004 | Simpson et al. |
| 2004/0172300 A1 | 9/2004 | Mihai et al. |
| 2004/0172301 A1 | 9/2004 | Mihai et al. |
| 2004/0172302 A1 | 9/2004 | Martucci et al. |
| 2004/0176667 A1 | 9/2004 | Mihai et al. |
| 2004/0224293 A1 | 11/2004 | Penning |
| 2004/0236240 A1 | 11/2004 | Kraus et al. |
| 2004/0249673 A1 | 12/2004 | Smith |
| 2005/0016534 A1 | 1/2005 | Ost |
| 2005/0033198 A1 | 2/2005 | Kehyayan et al. |
| 2005/0039748 A1 | 2/2005 | Andrieux |
| 2005/0054910 A1 | 3/2005 | Tremblay et al. |
| 2005/0055242 A1 | 3/2005 | Bello et al. |
| 2005/0055244 A1 | 3/2005 | Mullan et al. |
| 2005/0065817 A1 | 3/2005 | Mihai et al. |
| 2005/0075542 A1 | 4/2005 | Goldreich |
| 2005/0075904 A1 | 4/2005 | Wager |
| 2005/0085869 A1 | 4/2005 | Tehrani |
| 2005/0104860 A1 | 5/2005 | McCreary |
| 2005/0108057 A1 | 5/2005 | Cohen |
| 2005/0112013 A1 | 5/2005 | DeVries et al. |
| 2005/0112325 A1 | 5/2005 | Hickle |
| 2005/0124866 A1 | 6/2005 | Elaz |
| 2005/0133027 A1 | 6/2005 | Elaz |
| 2005/0137480 A1 | 6/2005 | Alt et al. |
| 2005/0139212 A1 | 6/2005 | Bourdon |
| 2005/0139213 A1 | 6/2005 | Blike |
| 2005/0143632 A1 | 6/2005 | Elaz |
| 2005/0156933 A1 | 7/2005 | Lee et al. |
| 2005/0171876 A1 | 8/2005 | Golden |
| 2005/0177096 A1 | 8/2005 | Bollish et al. |
| 2005/0188083 A1 | 8/2005 | Biondi |
| 2005/0192488 A1 | 9/2005 | Bryenton et al. |
| 2005/0204310 A1 | 9/2005 | De Zwart et al. |
| 2005/0215904 A1 | 9/2005 | Sumanaweera |
| 2005/0217674 A1 | 10/2005 | Burton et al. |
| 2005/0251040 A1 | 11/2005 | Relkuntwar |
| 2005/0267536 A1 * | 12/2005 | Freeman et al. .................. 607/5 |
| 2005/0288571 A1 | 12/2005 | Perkins |
| 2006/0047202 A1 | 3/2006 | Elliott |
| 2006/0078867 A1 | 4/2006 | Penny |
| 2006/0080140 A1 | 4/2006 | Buttner |
| 2006/0080343 A1 | 4/2006 | Carter |
| 2006/0102171 A1 | 5/2006 | Gavish |
| 2006/0122474 A1 | 6/2006 | Teller et al. |
| 2006/0129055 A1 | 6/2006 | Orr et al. |
| 2006/0144396 A1 | 7/2006 | DeVries |

(56) References Cited

U.S. PATENT DOCUMENTS

| | | |
|---|---|---|
| 2006/0149144 A1 | 7/2006 | Lynn et al. |
| 2006/0149589 A1 | 7/2006 | Wager |
| 2006/0150982 A1 | 7/2006 | Wood |
| 2006/0155183 A1 | 7/2006 | Kroecker |
| 2006/0155206 A1 | 7/2006 | Lynn |
| 2006/0155207 A1 | 7/2006 | Lynn et al. |
| 2006/0161071 A1 | 7/2006 | Lynn et al. |
| 2006/0173257 A1 | 8/2006 | Nagai et al. |
| 2006/0174884 A1 | 8/2006 | Habashi |
| 2006/0178911 A1 | 8/2006 | Syed et al. |
| 2006/0189880 A1 | 8/2006 | Lynn et al. |
| 2006/0189900 A1 | 8/2006 | Flaherty |
| 2006/0195041 A1 | 8/2006 | Lynn |
| 2006/0196507 A1 | 9/2006 | Bradley |
| 2006/0200009 A1 | 9/2006 | Wekell et al. |
| 2006/0211950 A1* | 9/2006 | Brunner et al. ............... 600/538 |
| 2006/0213518 A1 | 9/2006 | DeVries |
| 2006/0229822 A1 | 10/2006 | Theobald |
| 2006/0235324 A1 | 10/2006 | Lynn |
| 2006/0237015 A1 | 10/2006 | Berthon-Jones et al. |
| 2006/0249151 A1 | 11/2006 | Gambone |
| 2006/0249153 A1 | 11/2006 | DeVries et al. |
| 2006/0264762 A1 | 11/2006 | Starr |
| 2006/0278221 A1 | 12/2006 | Schermeier et al. |
| 2006/0278222 A1 | 12/2006 | Schermeier et al. |
| 2006/0293609 A1 | 12/2006 | Stahmann et al. |
| 2006/0294464 A1 | 12/2006 | Tokimoto et al. |
| 2007/0000490 A1 | 1/2007 | DeVries |
| 2007/0000494 A1 | 1/2007 | Banner et al. |
| 2007/0016441 A1 | 1/2007 | Stroup |
| 2007/0017515 A1 | 1/2007 | Wallace |
| 2007/0021673 A1 | 1/2007 | Arbel et al. |
| 2007/0028921 A1 | 2/2007 | Banner et al. |
| 2007/0038081 A1 | 2/2007 | Eck et al. |
| 2007/0060812 A1 | 3/2007 | Harel et al. |
| 2007/0062532 A1 | 3/2007 | Choncholas |
| 2007/0062533 A1 | 3/2007 | Choncholas et al. |
| 2007/0073181 A1 | 3/2007 | Pu |
| 2007/0077200 A1 | 4/2007 | Baker |
| 2007/0113849 A1 | 5/2007 | Matthews |
| 2007/0119453 A1 | 5/2007 | Lu et al. |
| 2007/0123758 A1 | 5/2007 | Miesel et al. |
| 2007/0123792 A1 | 5/2007 | Kline |
| 2007/0129647 A1 | 6/2007 | Lynn |
| 2007/0149860 A1 | 6/2007 | Lynn et al. |
| 2007/0156060 A1 | 7/2007 | Cervantes |
| 2007/0156456 A1 | 7/2007 | McGillin |
| 2007/0157931 A1 | 7/2007 | Parker |
| 2007/0163589 A1 | 7/2007 | DeVries |
| 2007/0179357 A1 | 8/2007 | Bardy |
| 2007/0185390 A1 | 8/2007 | Perkins et al. |
| 2007/0191697 A1 | 8/2007 | Lynn et al. |
| 2007/0199566 A1 | 8/2007 | Be'eri |
| 2007/0208438 A1 | 9/2007 | El-Mankabady et al. |
| 2007/0215155 A1 | 9/2007 | Marx et al. |
| 2007/0225574 A1 | 9/2007 | Ueda |
| 2007/0227537 A1 | 10/2007 | Bemister et al. |
| 2007/0229249 A1 | 10/2007 | McNeal |
| 2007/0241884 A1 | 10/2007 | Yamazaki |
| 2007/0265510 A1 | 11/2007 | Bardy |
| 2007/0265877 A1 | 11/2007 | Rice et al. |
| 2007/0271122 A1 | 11/2007 | Zaleski |
| 2007/0272241 A1 | 11/2007 | Sanborn et al. |
| 2007/0272242 A1 | 11/2007 | Sanborn |
| 2007/0273216 A1 | 11/2007 | Farbarik |
| 2007/0276439 A1 | 11/2007 | Miesel et al. |
| 2007/0284361 A1 | 12/2007 | Nadjafizadeh et al. |
| 2007/0293741 A1 | 12/2007 | Bardy |
| 2008/0000477 A1 | 1/2008 | Huster et al. |
| 2008/0000479 A1 | 1/2008 | Elaz |
| 2008/0007396 A1 | 1/2008 | Parkulo |
| 2008/0022215 A1 | 1/2008 | Lee et al. |
| 2008/0033661 A1 | 2/2008 | Syroid et al. |
| 2008/0039735 A1 | 2/2008 | Hickerson |
| 2008/0041380 A1 | 2/2008 | Wallace |
| 2008/0045844 A1 | 2/2008 | Arbel et al. |
| 2008/0047554 A1 | 2/2008 | Roy |
| 2008/0053438 A1 | 3/2008 | DeVries |
| 2008/0053441 A1 | 3/2008 | Gottlib et al. |
| 2008/0064963 A1 | 3/2008 | Schwaibold et al. |
| 2008/0065420 A1 | 3/2008 | Tirinato |
| 2008/0066753 A1 | 3/2008 | Martin et al. |
| 2008/0072896 A1 | 3/2008 | Setzer |
| 2008/0072900 A1 | 3/2008 | Kenyon et al. |
| 2008/0072901 A1 | 3/2008 | Habashi |
| 2008/0072902 A1 | 3/2008 | Setzer |
| 2008/0076970 A1 | 3/2008 | Foulis et al. |
| 2008/0077033 A1 | 3/2008 | Figueiredo |
| 2008/0077038 A1 | 3/2008 | McDonough et al. |
| 2008/0077436 A1 | 3/2008 | Muradia |
| 2008/0078390 A1 | 4/2008 | Milne |
| 2008/0083644 A1 | 4/2008 | Janbakhsh et al. |
| 2008/0086691 A1* | 4/2008 | Hopermann et al. ......... 715/736 |
| 2008/0091122 A1 | 4/2008 | Dunlop |
| 2008/0092043 A1 | 4/2008 | Trethewey |
| 2008/0092894 A1 | 4/2008 | Nicolazzi et al. |
| 2008/0097234 A1 | 4/2008 | Nicolazzi et al. |
| 2008/0103368 A1 | 5/2008 | Craine et al. |
| 2008/0110460 A1 | 5/2008 | Elaz |
| 2008/0125873 A1 | 5/2008 | Payne |
| 2008/0154100 A1* | 6/2008 | Thalmeier et al. ............ 600/301 |
| 2008/0161653 A1 | 7/2008 | Lin et al. |
| 2008/0172249 A1 | 7/2008 | Glaser-Seidnitzer |
| 2008/0178880 A1 | 7/2008 | Christopher |
| 2008/0178882 A1 | 7/2008 | Christopher |
| 2008/0183057 A1 | 7/2008 | Taube |
| 2008/0185009 A1 | 8/2008 | Choncholas |
| 2008/0205427 A1 | 8/2008 | Jost |
| 2008/0208012 A1 | 8/2008 | Ali |
| 2008/0214947 A1 | 9/2008 | Hunt |
| 2008/0230057 A1 | 9/2008 | Sutherland |
| 2008/0236582 A1 | 10/2008 | Tehrani |
| 2008/0236585 A1 | 10/2008 | Parker |
| 2008/0243016 A1 | 10/2008 | Liao et al. |
| 2008/0251070 A1 | 10/2008 | Pinskiy |
| 2008/0255880 A1 | 10/2008 | Beller |
| 2008/0258929 A1 | 10/2008 | Maschke |
| 2008/0270912 A1 | 10/2008 | Booth |
| 2008/0281219 A1 | 11/2008 | Glickman et al. |
| 2008/0293025 A1 | 11/2008 | Zamierowsi |
| 2008/0295830 A1 | 12/2008 | Martonen |
| 2008/0295839 A1 | 12/2008 | Habashi |
| 2008/0306351 A1 | 12/2008 | Izumi |
| 2008/0308109 A1 | 12/2008 | Brain |
| 2008/0312954 A1 | 12/2008 | Ullrich |
| 2008/0319513 A1 | 12/2008 | Pu |
| 2009/0005651 A1 | 1/2009 | Ward |
| 2009/0007909 A1 | 1/2009 | Carrico |
| 2009/0038921 A1 | 2/2009 | Kaps et al. |
| 2009/0054743 A1 | 2/2009 | Stewart |
| 2009/0055735 A1 | 2/2009 | Zaleski |
| 2009/0062725 A1 | 3/2009 | Goebel |
| 2009/0063181 A1 | 3/2009 | Nho |
| 2009/0065004 A1 | 3/2009 | Childers et al. |
| 2009/0076342 A1 | 3/2009 | Amurthur et al. |
| 2009/0124917 A1 | 5/2009 | Hatlestad et al. |
| 2009/0125333 A1 | 5/2009 | Heywood |
| 2009/0126734 A1 | 5/2009 | Dunsmore |
| 2009/0131758 A1 | 5/2009 | Heywood |
| 2009/0133701 A1 | 5/2009 | Brain |
| 2009/0143694 A1 | 6/2009 | Krauss et al. |
| 2009/0145438 A1 | 6/2009 | Brain |
| 2009/0149200 A1 | 6/2009 | Jayasinghe |
| 2009/0149723 A1 | 6/2009 | Krauss et al. |
| 2009/0149743 A1* | 6/2009 | Barron et al. ................. 600/431 |
| 2009/0149927 A1 | 6/2009 | Kneuer |
| 2009/0150184 A1 | 6/2009 | Spahn |
| 2009/0165795 A1 | 7/2009 | Nadjafizadeh et al. |
| 2009/0171167 A1 | 7/2009 | Baker, Jr. |
| 2009/0171176 A1 | 7/2009 | Andersohn |
| 2009/0192421 A1 | 7/2009 | Huster et al. |
| 2009/0205661 A1 | 8/2009 | Stephenson et al. |
| 2009/0205663 A1 | 8/2009 | Vandine et al. |
| 2009/0209828 A1 | 8/2009 | Musin |

(56) References Cited

U.S. PATENT DOCUMENTS

| | | |
|---|---|---|
| 2009/0209849 A1 | 8/2009 | Rowe |
| 2009/0216145 A1 | 8/2009 | Skerl et al. |
| 2009/0221926 A1 | 9/2009 | Younes |
| 2009/0240523 A1 | 9/2009 | Friedlander |
| 2009/0241952 A1 | 10/2009 | Nicolazzi |
| 2009/0241953 A1 | 10/2009 | Vandine et al. |
| 2009/0241956 A1 | 10/2009 | Baker, Jr. |
| 2009/0241957 A1 | 10/2009 | Baker, Jr. |
| 2009/0241958 A1 | 10/2009 | Baker, Jr. |
| 2009/0241962 A1 | 10/2009 | Jafari et al. |
| 2009/0244003 A1 | 10/2009 | Bonnat |
| 2009/0247849 A1 | 10/2009 | McCutcheon et al. |
| 2009/0247853 A1 | 10/2009 | Debreczeny |
| 2009/0247891 A1 | 10/2009 | Wood |
| 2009/0249247 A1 | 10/2009 | Tseng et al. |
| 2009/0250054 A1 | 10/2009 | Loncar |
| 2009/0301486 A1 | 12/2009 | Masic |
| 2009/0301487 A1 | 12/2009 | Masic |
| 2009/0301490 A1 | 12/2009 | Masic |
| 2009/0301491 A1 | 12/2009 | Masic et al. |
| 2010/0004517 A1 | 1/2010 | Bryenton et al. |
| 2010/0011307 A1 | 1/2010 | Desfossez et al. |
| 2010/0022904 A1 | 1/2010 | Centen |
| 2010/0024820 A1 | 2/2010 | Bourdon |
| 2010/0030092 A1 | 2/2010 | Kristensen et al. |
| 2010/0048985 A1 | 2/2010 | Henke et al. |
| 2010/0048986 A1 | 2/2010 | Henke et al. |
| 2010/0049034 A1 | 2/2010 | Eck et al. |
| 2010/0049264 A1 | 2/2010 | Henke et al. |
| 2010/0049265 A1 | 2/2010 | Henke et al. |
| 2010/0051026 A1 | 3/2010 | Graboi |
| 2010/0051029 A1 | 3/2010 | Jafari et al. |
| 2010/0056852 A1 | 3/2010 | Henke et al. |
| 2010/0056853 A1 | 3/2010 | Henke et al. |
| 2010/0056855 A1 | 3/2010 | Henke et al. |
| 2010/0056929 A1 | 3/2010 | Stahmann et al. |
| 2010/0056941 A1 | 3/2010 | Henke et al. |
| 2010/0056942 A1 | 3/2010 | Henke et al. |
| 2010/0057148 A1 | 3/2010 | Henke et al. |
| 2010/0059061 A1 | 3/2010 | Brain |
| 2010/0063348 A1 | 3/2010 | Henke et al. |
| 2010/0063350 A1 | 3/2010 | Henke et al. |
| 2010/0063365 A1 | 3/2010 | Pisani et al. |
| 2010/0069761 A1 | 3/2010 | Karst et al. |
| 2010/0069774 A1 | 3/2010 | Bingham et al. |
| 2010/0071689 A1 | 3/2010 | Thiessen |
| 2010/0071692 A1 | 3/2010 | Porges |
| 2010/0071695 A1 | 3/2010 | Thiessen |
| 2010/0071696 A1 | 3/2010 | Jafari |
| 2010/0071697 A1 | 3/2010 | Jafari et al. |
| 2010/0072055 A1 | 3/2010 | Tanaka et al. |
| 2010/0076278 A1 | 3/2010 | van Der Zande et al. |
| 2010/0078017 A1 | 4/2010 | Andrieux et al. |
| 2010/0078026 A1 | 4/2010 | Andrieux et al. |
| 2010/0081119 A1 | 4/2010 | Jafari et al. |
| 2010/0081890 A1 | 4/2010 | Li et al. |
| 2010/0081955 A1 | 4/2010 | Wood, Jr. et al. |
| 2010/0083968 A1 | 4/2010 | Wondka et al. |
| 2010/0095961 A1 | 4/2010 | Tornesel et al. |
| 2010/0130873 A1 | 5/2010 | Yuen et al. |
| 2010/0139660 A1 | 6/2010 | Adahan |
| 2010/0147303 A1 | 6/2010 | Jafari et al. |
| 2010/0160839 A1 | 6/2010 | Freeman et al. |
| 2010/0186744 A1 | 7/2010 | Andrieux |
| 2010/0218765 A1 | 9/2010 | Jafari et al. |
| 2010/0218766 A1 | 9/2010 | Milne |
| 2010/0218767 A1 | 9/2010 | Jafari et al. |
| 2010/0236555 A1 | 9/2010 | Jafari et al. |
| 2010/0242961 A1 | 9/2010 | Mougel et al. |
| 2010/0249549 A1 | 9/2010 | Baker, Jr. et al. |
| 2010/0274100 A1 | 10/2010 | Behar et al. |
| 2010/0275920 A1* | 11/2010 | Tham et al. ............. 128/204.23 |
| 2010/0282259 A1 | 11/2010 | Figueiredo et al. |
| 2010/0288283 A1 | 11/2010 | Campbell et al. |
| 2010/0298718 A1 | 11/2010 | Gilham et al. |
| 2010/0300446 A1 | 12/2010 | Nicolazzi et al. |
| 2010/0312132 A1 | 12/2010 | Wood et al. |
| 2010/0317980 A1 | 12/2010 | Guglielmino |
| 2011/0004489 A1 | 1/2011 | Schoenberg et al. |
| 2011/0009746 A1 | 1/2011 | Tran et al. |
| 2011/0011400 A1 | 1/2011 | Gentner et al. |
| 2011/0015493 A1 | 1/2011 | Koschek |
| 2011/0023878 A1 | 2/2011 | Thiessen |
| 2011/0023879 A1 | 2/2011 | Vandine et al. |
| 2011/0023880 A1 | 2/2011 | Thiessen |
| 2011/0023881 A1 | 2/2011 | Thiessen |
| 2011/0029910 A1 | 2/2011 | Thiessen |
| 2011/0041849 A1 | 2/2011 | Chen et al. |
| 2011/0041850 A1 | 2/2011 | Vandine et al. |
| 2011/0054289 A1 | 3/2011 | Derchak et al. |
| 2011/0055720 A1* | 3/2011 | Potter et al. .................... 715/747 |
| 2011/0098638 A1* | 4/2011 | Chawla et al. .................. 604/66 |
| 2011/0126151 A1 | 5/2011 | Bean et al. |
| 2011/0126829 A1 | 6/2011 | Carter et al. |
| 2011/0126832 A1 | 6/2011 | Winter et al. |
| 2011/0126834 A1 | 6/2011 | Winter et al. |
| 2011/0126835 A1 | 6/2011 | Winter et al. |
| 2011/0126836 A1 | 6/2011 | Winter et al. |
| 2011/0126837 A1 | 6/2011 | Winter et al. |
| 2011/0128008 A1 | 6/2011 | Carter |
| 2011/0132361 A1 | 6/2011 | Sanchez |
| 2011/0132362 A1 | 6/2011 | Sanchez |
| 2011/0132364 A1 | 6/2011 | Ogilvie et al. |
| 2011/0132365 A1 | 6/2011 | Patel et al. |
| 2011/0132366 A1 | 6/2011 | Ogilvie et al. |
| 2011/0132367 A1 | 6/2011 | Patel |
| 2011/0132368 A1 | 6/2011 | Sanchez et al. |
| 2011/0132369 A1 | 6/2011 | Sanchez |
| 2011/0132371 A1 | 6/2011 | Sanchez et al. |
| 2011/0133936 A1 | 6/2011 | Sanchez et al. |
| 2011/0138308 A1 | 6/2011 | Palmer et al. |
| 2011/0138309 A1 | 6/2011 | Skidmore et al. |
| 2011/0138311 A1 | 6/2011 | Palmer |
| 2011/0138323 A1 | 6/2011 | Skidmore et al. |
| 2011/0146681 A1 | 6/2011 | Jafari et al. |
| 2011/0146683 A1 | 6/2011 | Jafari et al. |
| 2011/0154241 A1 | 6/2011 | Skidmore et al. |
| 2011/0175728 A1 | 7/2011 | Baker, Jr. |
| 2011/0196251 A1 | 8/2011 | Jourdain et al. |
| 2011/0209702 A1 | 9/2011 | Vuong et al. |
| 2011/0209704 A1 | 9/2011 | Jafari et al. |
| 2011/0209707 A1 | 9/2011 | Terhark |
| 2011/0213215 A1 | 9/2011 | Doyle et al. |
| 2011/0259330 A1 | 10/2011 | Jafari et al. |
| 2011/0259332 A1 | 10/2011 | Sanchez et al. |
| 2011/0259333 A1 | 10/2011 | Sanchez et al. |
| 2011/0265024 A1 | 10/2011 | Leone et al. |
| 2011/0271960 A1 | 11/2011 | Milne et al. |
| 2011/0273299 A1 | 11/2011 | Milne et al. |
| 2012/0000467 A1 | 1/2012 | Milne et al. |
| 2012/0000468 A1 | 1/2012 | Milne et al. |
| 2012/0000469 A1 | 1/2012 | Milne et al. |
| 2012/0000470 A1 | 1/2012 | Milne et al. |
| 2012/0029317 A1 | 2/2012 | Doyle et al. |
| 2012/0030611 A1 | 2/2012 | Skidmore |
| 2012/0060841 A1 | 3/2012 | Crawford, Jr. et al. |
| 2012/0066609 A1* | 3/2012 | Howard et al. ................ 715/738 |
| 2012/0071729 A1 | 3/2012 | Doyle et al. |
| 2012/0090611 A1 | 4/2012 | Graboi et al. |
| 2012/0096381 A1 | 4/2012 | Milne et al. |
| 2012/0133519 A1 | 5/2012 | Milne et al. |
| 2012/0136222 A1 | 5/2012 | Doyle et al. |
| 2012/0137249 A1 | 5/2012 | Milne et al. |
| 2012/0137250 A1 | 5/2012 | Milne et al. |

FOREIGN PATENT DOCUMENTS

| | | |
|---|---|---|
| EP | 1421966 | 5/2004 |
| EP | 1464357 | 10/2004 |
| GB | 2319967 | 6/1998 |
| WO | WO9014852 A1 | 12/1990 |
| WO | WO9308534 A1 | 4/1993 |
| WO | WO9312823 A2 | 7/1993 |
| WO | WO9314696 A1 | 8/1993 |

(56) References Cited

FOREIGN PATENT DOCUMENTS

| | | |
|---|---|---|
| WO | WO9414374 A1 | 7/1994 |
| WO | WO9508471 A1 | 3/1995 |
| WO | WO9532480 A1 | 11/1995 |
| WO | WO9624285 A1 | 8/1996 |
| WO | WO 9706843 A1 * | 2/1997 |
| WO | WO9720592 A1 | 6/1997 |
| WO | WO9811840 A1 | 3/1998 |
| WO | WO9814116 A2 | 4/1998 |
| WO | WO9829790 A2 | 7/1998 |
| WO | WO9833554 A1 | 8/1998 |
| WO | 9841267 A1 | 9/1998 |
| WO | WO9840014 A1 | 9/1998 |
| WO | WO9841267 C1 | 9/1998 |
| WO | WO9841269 A1 | 9/1998 |
| WO | WO9841270 A1 | 9/1998 |
| WO | WO9841271 A1 | 9/1998 |
| WO | WO9858219 A1 | 12/1998 |
| WO | WO9903524 A1 | 1/1999 |
| WO | WO9952431 A1 | 10/1999 |
| WO | WO9952437 A1 | 10/1999 |
| WO | WO9959460 A2 | 11/1999 |
| WO | WO9962403 A1 | 12/1999 |
| WO | WO0018293 A1 | 4/2000 |
| WO | WO0019886 A1 | 4/2000 |
| WO | WO0062664 A1 | 10/2000 |
| WO | WO0100264 A1 | 1/2001 |
| WO | WO0100265 A1 | 1/2001 |
| WO | WO0128416 A1 | 4/2001 |
| WO | WO0134022 A1 | 5/2001 |
| WO | WO0245566 A2 | 6/2002 |
| WO | WO02082967 A2 | 10/2002 |
| WO | WO03015005 A2 | 2/2003 |
| WO | WO03024317 A2 | 3/2003 |
| WO | WO03045493 A2 | 6/2003 |
| WO | WO03053503 A1 | 7/2003 |
| WO | WO03060650 A2 | 7/2003 |
| WO | WO03060651 A2 | 7/2003 |
| WO | WO03075989 A2 | 9/2003 |
| WO | WO03075990 A2 | 9/2003 |
| WO | WO03075991 A1 | 9/2003 |
| WO | WO03084405 A2 | 10/2003 |
| WO | WO2004014216 A2 | 2/2004 |
| WO | WO2004014226 A1 | 2/2004 |
| WO | WO2004032719 A2 | 4/2004 |
| WO | WO2004043254 A1 | 5/2004 |
| WO | WO2005010796 | 2/2005 |
| WO | WO2005024729 A1 | 3/2005 |
| WO | WO2005055825 A1 | 6/2005 |
| WO | WO2005056087 A1 | 6/2005 |
| WO | WO2005069740 A2 | 8/2005 |
| WO | WO2005077260 A1 | 8/2005 |
| WO | WO2005112739 A1 | 12/2005 |
| WO | WO2006008745 A2 | 1/2006 |
| WO | WO2006009830 A2 | 1/2006 |
| WO | WO2006037184 A1 | 4/2006 |
| WO | WO2006050388 A2 | 5/2006 |
| WO | WO2006051466 A1 | 5/2006 |
| WO | WO2006078432 A2 | 7/2006 |
| WO | WO2006094055 A2 | 9/2006 |
| WO | WO2006096080 A1 | 9/2006 |
| WO | WO2006109072 A2 | 10/2006 |
| WO | WO2006123956 A1 | 11/2006 |
| WO | WO2006125986 A1 | 11/2006 |
| WO | WO2006125987 A1 | 11/2006 |
| WO | WO2006125989 A1 | 11/2006 |
| WO | WO2006125990 A1 | 11/2006 |
| WO | WO2006137067 A2 | 12/2006 |
| WO | WO2007033050 A2 | 3/2007 |
| WO | WO2007106804 A2 | 9/2007 |
| WO | WO 2007145948 | 12/2007 |
| WO | WO2008030091 A1 | 3/2008 |
| WO | WO2008042699 A2 | 4/2008 |
| WO | WO2008058997 A2 | 5/2008 |
| WO | WO2008062554 A1 | 5/2008 |
| WO | WO2008113410 A1 | 9/2008 |
| WO | WO2008118951 A1 | 10/2008 |
| WO | WO2008140528 A1 | 11/2008 |
| WO | WO2008146264 A2 | 12/2008 |
| WO | WO2008148134 A1 | 12/2008 |
| WO | WO2009024967 A2 | 2/2009 |
| WO | WO2009027864 A1 | 3/2009 |
| WO | WO2009036334 A1 | 3/2009 |
| WO | WO2009124297 A1 | 10/2009 |
| WO | WO2010009531 A1 | 1/2010 |
| WO | WO2010020980 A1 | 2/2010 |
| WO | WO2010021730 A1 | 2/2010 |
| WO | WO2010039989 A1 | 4/2010 |
| WO | WO2010126916 A1 | 11/2010 |
| WO | WO2010141415 A1 | 12/2010 |
| WO | WO2011005953 A2 | 1/2011 |
| WO | WO2011022242 A1 | 2/2011 |

OTHER PUBLICATIONS

7200 Series Ventilator, Options, and Accessories: Operator's Manual. Nellcor Puritan Bennett, Part No. 22300 A, Sep. 1990, pp. 1-196.

7200 Ventilatory System: Addendum/Errata. Nellcor Puritan Bennett, Part No. 4-023576-00, Rev. A, Apr. 1988, pp. 1-32.

800 Operator's and Technical Reference Manual. Series Ventilator System, Nellcor Puritan Bennett, Part No. 4-070088-00, Rev. L, Aug. 2010, pp. 1-476.

840 Operator's and Technical Reference Manual. Ventilator System, Nellcor Puritan Bennett, Part No. 4-075609-00, Rev. G, Oct. 2006, pp. 1-424.

PCT International Search Report and Written Opinion in Application PCT/US2010/058131, mailed May 18, 2011, 12 pgs.

PCT International Search Report mailed Apr. 7, 2011, Applicant's Reference H-RM-01984WO, International Application No. PCT/US2010/060871, International Filing Date Dec. 16, 2010, Applicant Nellcor Puritan Bennett LLC, 3 pgs.

U.S. Appl. No. 12/631,685, Office Action mailed Nov. 15, 2011, 22 pgs.

U.S. Appl. No. 12/631,685, Office Action mailed Feb. 29, 2012, 23 pgs.

U.S. Appl. No. 12/631,712, Office Action mailed Nov. 14, 2011, 20 pgs.

U.S. Appl. No. 12/631,712, Office Action mailed Feb. 29, 2012, 22 pgs.

U.S. Appl. No. 12/631,750, Office Action mailed Dec. 8, 2011, 12 pgs.

U.S. Appl. No. 12/631,752, Office Action mailed Dec. 8, 2011, 12 pgs.

U.S. Appl. No. 12/970,696, Notice of Allowance mailed Jan. 15, 2013, 14 pgs.

U.S. Appl. No. 12/844,579, Advisory Action mailed Feb. 14, 2013, 3 pgs.

U.S. Appl. No. 12/631,750, Advisory Action mailed Jun. 21, 2013, 3 pgs.

U.S. Appl. No. 12/631,750, Office Action mailed Mar. 25, 2013, 15 pgs.

U.S. Appl. No. 12/844,579, Notice of Allowance mailed Mar. 26, 2013, 6 pgs.

U.S. Appl. No. 12/631,750, Office Action mailed Oct. 4, 2012, 13 pgs.

U.S. Appl. No. 12/844,579, Office Action mailed Aug. 30, 2012, 9 pgs.

U.S. Appl. No. 12/844,579, Office Action mailed Dec. 19, 2012, 8 pgs.

U.S. Appl. No. 12/631,685, Advisory Action mailed May 11, 2012, 3 pgs.

U.S. Appl. No. 12/631,712, Advisory Action mailed May 11, 2012, 3 pgs.

U.S. Appl. No. 12/631,750, Advisory Action mailed Jul. 24, 2012, 3 pgs.

U.S. Appl. No. 12/631,750, Office Action mailed May 16, 2012, 13 pgs.

U.S. Appl. No. 12/631,752, Notice of Allowance mailed Jun. 11, 2012, 8 pgs.

U.S. Appl. No. 12/631,752, Notice of Allowance mailed Jul. 24, 2012, 8 pgs.

(56) References Cited

OTHER PUBLICATIONS

U.S. Appl. No. 12/631,752, Office Action mailed Mar. 15, 2012, 13 pgs.

U.S. Appl. No. 12/970,696, Office Action mailed Aug. 2, 2012, 12 pgs.

US 7,284,551, 10/2007, Jones et al. (withdrawn)

* cited by examiner

QUICK INITIATION OF RESPIRATORY SUPPORT VIA A VENTILATOR USER INTERFACE

RELATED APPLICATIONS

This application claims the benefit of U.S. Provisional Patent Application Ser. No. 61/266,953, filed Dec. 4, 2009, which application is hereby incorporated by reference. This application is related to co-owned U.S. patent application Ser. No. 12/631,752 (now U.S. Pat. No. 8,335,992) entitled "Visual Indication of Settings Changes on a Ventilator Graphical User Interface"; U.S. patent application Ser. No. 12/631,750 (now U.S. Pat. No. 8,924,878) entitled "Display and Access to Settings on a Ventilator Graphical User Interface"; U.S. patent application Ser. No. 12/631,712 entitled "Display of Respiratory Data on a Ventilator Graphical User Interface"; and U.S. patent application Ser. No. 12/631,685 entitled "Visual Indication of Alarms on a Ventilator Graphical User Interface"; all filed on Dec. 4, 2009, the entire disclosures of all of which are hereby incorporated herein by reference.

INTRODUCTION

A ventilator is a device that mechanically helps patients breathe by replacing some or all of the muscular effort required to inflate and deflate the lungs. A ventilator may be configured with various settings and parameters for proper delivery of respiratory support. Indeed, many of the settings and/or parameters typically must be configured and input by a clinician prior to ventilation. In fact, in many cases, clinicians may be required to repeatedly enter the same settings and parameters manually for each new patient because they are based on uniform protocols or other specifications.

Quick Initiation of Respiratory Support Via a Ventilator User Interface

This disclosure describes improved systems and methods for efficiently configuring respiratory support settings and/or parameters in a ventilatory system. Specifically, the present methods and user interface provide an efficient and consistent means for configuring ventilatory settings for a new patient. For instance, the ventilator may be preconfigured with appropriate parameter settings based on an institution-specific protocol, a physician-specific protocol, or other suitable protocol. Indeed, the present disclosure provides an institution and/or clinician with increased control over routine ventilatory settings by pre-configuring the ventilator with these settings. Further, the present disclosure may increase the consistent application of the routine ventilatory settings by eliminating repeated data entry by clinicians, decreasing the chances of error.

In addition, ventilation may be quickly and efficiently initiated for a new patient. As such, rather than inputting multiple parameter settings and data prior to initiating respiration, ventilatory initiation may be streamlined based on a minimal-step setup method. For instance, a clinician may select setup for a new patient and may merely input the patient's predicted body weight, the patient's gender and height, or other ratiometric patient data. These few inputs may be associated with numerous protocol-specific parameter settings that are appropriate for that patient's general weight or gender and height, for instance. Thereafter, the clinician may merely touch, or otherwise select, a quick-start element to initiate ventilation. Thus, preconfigured, protocol-specific settings may be efficiently and promptly applied to the ventilatory support of a new patient.

Embodiments of the present disclosure may recite ventilator user interfaces for providing minimal-step ventilation setup for a patient. Specifically, a ventilator may be configured with a computer having a user interface including a graphical user interface for accepting commands and for displaying information. The user interface may comprise at least one window associated with the user interface and one or more elements within the at least one window. The one or more elements may further comprise one or more input elements for inputting patient data and a selection element for initiating ventilation according to a quick-start method. The one or more input elements may further comprise an input element for inputting patient predicted body weight, one or more input elements for inputting patient gender and height, one or more input elements for inputting a patient gender and forearm length, or one or more input elements for inputting a patient gender and a distance from the patient's suprasternal notch to the patient's umbilicus.

These and various other features as well as advantages which characterize the systems and methods described herein will be apparent from a reading of the following detailed description and a review of the associated drawings. Additional features are set forth in the description which follows, and in part will be apparent from the description, or may be learned by practice of the technology. The benefits and features of the technology will be realized and attained by the structure particularly pointed out in the written description and claims hereof as well as the appended drawings.

It is to be understood that both the foregoing general description and the following detailed description are exemplary and explanatory and are intended to provide further explanation of the invention as claimed,

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following drawing figures, which form a part of this application, are illustrative of described technology and are not meant to limit the scope of the invention as claimed in any manner, which scope shall be based on the claims appended hereto.

DETAILED DESCRIPTION

Figure 1:
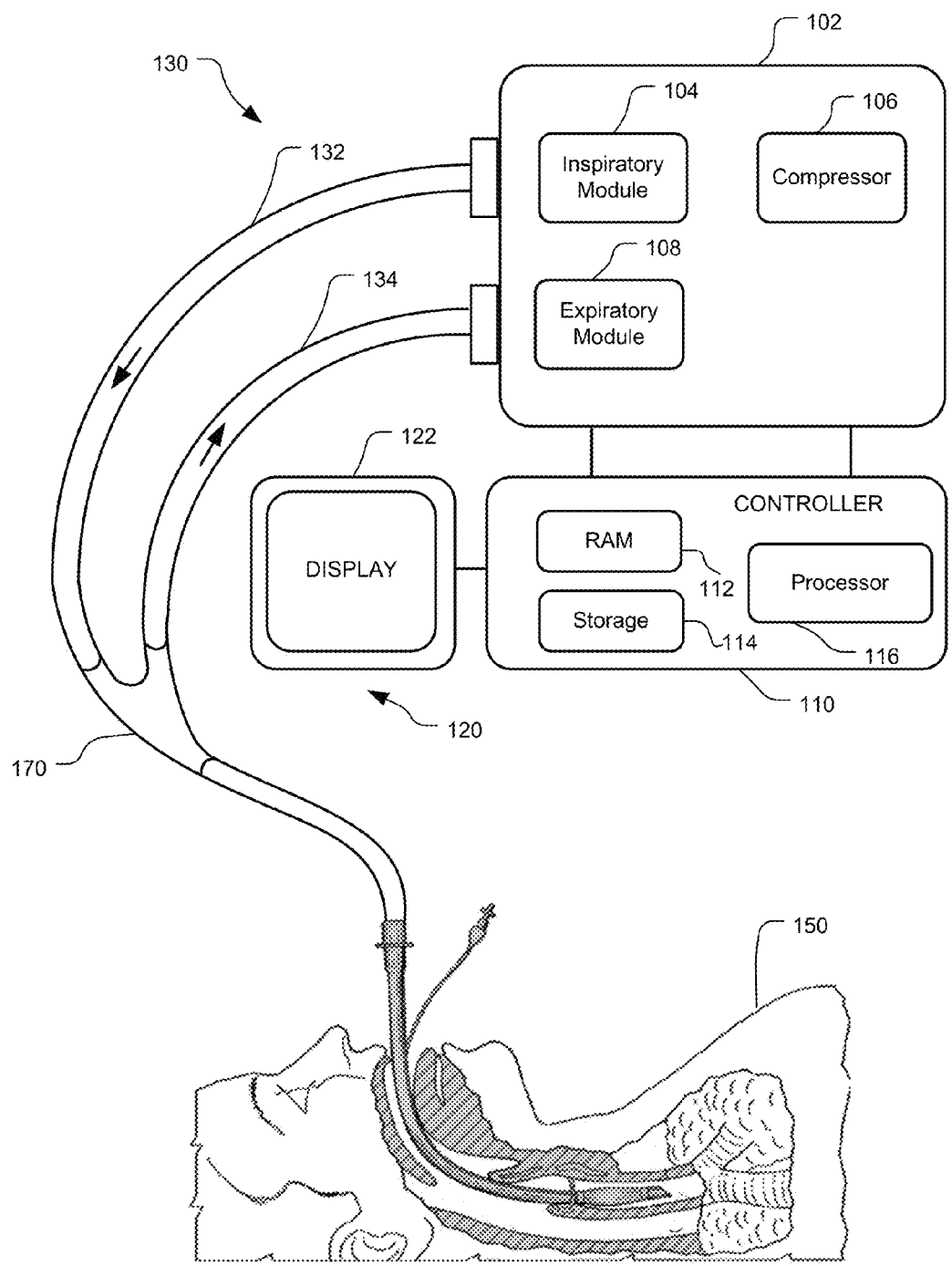
FIG. 1 is a diagram illustrating an embodiment of an exemplary ventilator connected to a human patient.

Although the techniques introduced above and discussed in detail below may be implemented for a variety of medical devices, the present disclosure will discuss the implementation of these techniques for use in a mechanical ventilator system. The reader will understand that the technology described in the context of a ventilator system could be adapted for use with other therapeutic equipment having user interfaces, including graphical user interfaces (GUIs), for prompt startup of a therapeutic treatment.

This disclosure describes systems and methods for efficiently and promptly initiating ventilation for a new patient in a ventilatory system. Specifically, embodiments may provide a user interface, including a graphical user interface or other display interface, for selecting a ventilatory setup menu for a new patient. The ventilatory setup menu may provide one or more options for a "quick" startup for the new patient. For instance, the ventilator may provide a clinician with an input element for entering a predicted body weight. Upon entering the predicted body weight, appropriate preconfigured parameter and mode settings may appear on the interface as pending default parameter settings. Thereafter, when the clinician selects a "Quick-Start" element, or other control indicating a prompt ventilatory startup, the pending preconfigured parameter settings may be accepted and ventilation may be initiated based on the preconfigured settings. Alternatively, the ventilator setup menu may provide a clinician with an input element for entering a patient gender and height. Upon entering the patient gender and height, appropriate preconfigured modes and parameter settings may appear on the interface as pending mode and parameter settings. Again, when the clinician selects a "Quick-Start" element, the pending preconfigured mode and parameter settings may be accepted and ventilation may be initiated based on the preconfigured settings. Additional input elements may also be provided within the spirit of the present invention. For example, one or more input elements for entering a patient gender and forearm length, or a patient gender and a distance from the patient's suprasternal notch to the umbilicus, or any other patient data suitable for correlation to protocol-specific modes and settings.

As such, the present disclosure provides an institution or clinician with optimal control over routine ventilatory settings. Specifically, routine settings may be preconfigured according to a hospital-specific, clinic-specific, physician-specific, or any other appropriate protocol. Parameter settings may be further associated with patient weight, patient gender and height, or any other patient-related ratio-metric variable, such that appropriate settings may be quickly and uniformly applied to new patients. Although parameter settings may be changed and edited in response to a particular patient's changing needs and/or condition, the present disclosure enables a quick and efficient initial setup procedure for a plurality of new patients. Indeed, many institutions generally mandate routine parameter settings upon setup based on weight or gender and height, yet these routine parameter settings are manually re-entered for each patient by a clinician.

FIG. 1 illustrates an embodiment of a ventilator connected to a human patient 150. The ventilator includes a pneumatic system 102 (also referred to as a pressure generating system 102) for circulating breathing gases to and from patient 150 via the ventilation tubing system 130, which couples the patient to the pneumatic system via an invasive patient interface (e.g., endotracheal tube).

Ventilation tubing system 130 may be a two-limb (shown) or a one-limb circuit for carrying gas to and from the patient 150. In a two-limb embodiment as shown, a fitting, typically referred to as a "wye-fitting" 170, may be provided to couple the patient interface to an inspiratory limb 132 and an expiratory limb 134 of the ventilation tubing system 130.

Pneumatic system 102 may be configured in a variety of ways. In the present example, system 102 includes an expiratory module 108 coupled with the expiratory limb 134 and an inspiratory module 104 coupled with the inspiratory limb 132. Compressor 106 or other source(s) of pressurized gases (e.g., air, oxygen, and/or helium) is coupled with inspiratory module 104 to provide a gas source for ventilatory support via inspiratory limb 132.

The pneumatic system may include a variety of other components, including sources for pressurized air and/or oxygen, mixing modules, valves, sensors, tubing, accumulators, filters, etc. Controller 110 is operatively coupled with pneumatic system 102, signal measurement and acquisition systems, and an operator interface 120 that may enable an operator to interact with the ventilator (e.g., reset alarms, change ventilator settings, select operational modes, view monitored parameters, etc.). Controller 110 may include memory 112, one or more processors 116, storage 114, and/or other components of the type commonly found in command and control computing devices.

The memory 112 is computer-readable storage media that stores software that is executed by the processor 116 and which controls the operation of the ventilator. In an embodiment, the memory 112 includes one or more solid-state storage devices such as flash memory chips. In an alternative embodiment, the memory 112 may be mass storage connected to the processor 116 through a mass storage controller (not shown) and a communications bus (not shown). Although the description of computer-readable media contained herein refers to a solid-state storage, it should be appreciated by those skilled in the art that computer-readable storage media can be any available media that can be accessed by the processor 116. Computer-readable storage media includes volatile and non-volatile, removable and non-removable media implemented in any method or technology for storage of information such as computer-readable instructions, data structures, program modules or other data. Computer-readable storage media includes, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by the computer.

As described in more detail below, controller 110 may monitor pneumatic system 102 in order to evaluate the condition of the patient and to ensure proper functioning of the ventilator based on various parameter settings. The specific parameter settings may be based on preconfigured settings applied to the controller 110, or based on input received via operator interface 120 and/or other components of the ventilator. In the depicted example, operator interface 120 includes a display 122 that is touch-sensitive, enabling the display to serve both as an input and output device.

Figure 2:
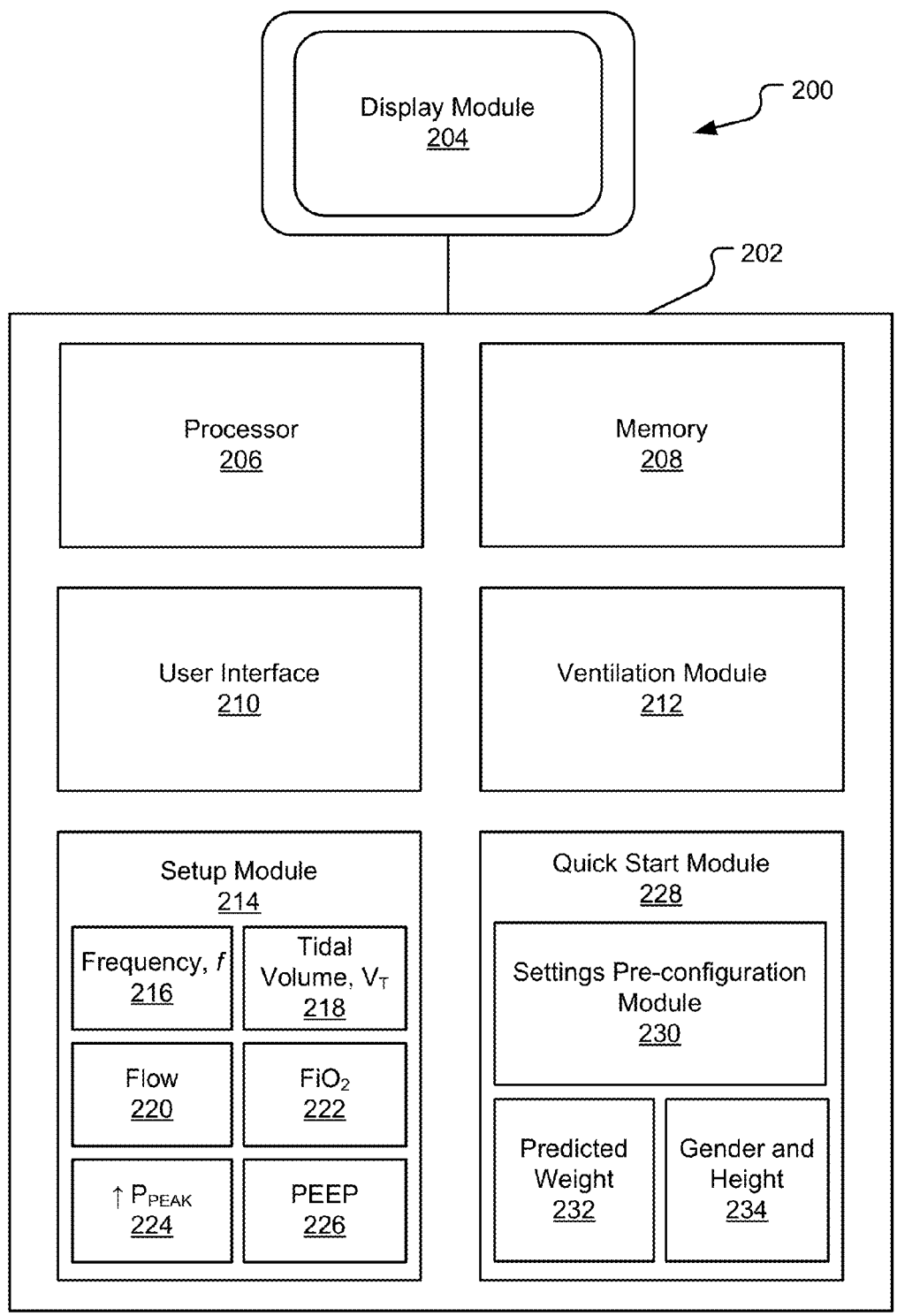
FIG. 2 is a block-diagram illustrating an embodiment of a ventilatory system having a user interface for efficiently and uniformly configuring ventilation setup for a new patient.

FIG. 2 is a block-diagram illustrating an embodiment of a ventilatory system having a user interface for efficiently and uniformly configuring ventilation setup for a new patient.

The ventilator 202 includes a display module 204, memory 208, one or more processors 206, user interface 210, and ventilation module 212. Memory 208 is defined as described above for memory 112. Similarly, the one or more processors 206 are defined as described above for the one or more processors 116.

Ventilation module 212 may oversee ventilation as delivered to a new patient according to appropriate parameter settings preconfigured according to any suitable protocol or specification. Alternatively, ventilation module 212 may oversee ventilation for a patient according to custom ventilatory settings, as determined appropriate by a clinician or institution and as manually input via user interface 210, or otherwise. For example, ventilation module 212 may monitor and regulate pressure delivery by any suitable method, either currently known or disclosed in the future, according to pressure parameter settings. Specifically, ventilation module 212 may be in communication with pneumatic system 102, including inspiratory module 104 coupled with inspiratory limb 132, and with compressor 106 or other source(s) of pressurized gases (e.g., air, oxygen, and/or helium). Compressor 106 may be coupled with inspiratory module 104, to provide a gas source for delivering air pressure via inspiratory limb 132. Ventilation module 212 may also be in communication with the setup module 214 and/or quick-start module 228 to deliver ventilation to a new patient according to appropriate parameter settings preconfigured according to any suitable protocol, for instance an institution-specific protocol.

The display module 204 presents various input screens and displays to a clinician, including but not limited to one or more setup screens, as will be described further herein, for promptly initiating ventilation for a new patient. The display module 204 is further configured to communicate with user interface 210. The display module 204 may provide a graphical user interface (GUI), providing various windows and elements to the clinician for input and interface command operations. User interface 210 may accept commands and input through display module 204 and may provide setup options to the clinician through a GUI on display module 204. Display module 204 may further be an interactive display, whereby the clinician may both receive and communicate information to the ventilator 202, as by a touch-activated user interface. Alternatively, user interface 210 may provide other suitable means of communication with the ventilator 202, for instance by a keyboard or other suitable interactive device.

The setup options provided to the clinician through the user interface may include, among others, options for initiating ventilation for a new patient. Specifically, the user interface may allow a clinician to manually configure parameter settings for a patient, or to rely on protocol-specific parameter settings for promptly initiating ventilation for a patient. As such, setup module 214 may accept input values from a clinician for configuring the various setup modules 216-226 or may accept values preconfigured according to a suitable institution-specific, physician-specific, or other protocol. Setup module 214 may further be in communication with ventilation module 212 and quick-start module 228. For instance, setup module 214 may communicate parameter settings to ventilation module 212 such that the ventilator may properly monitor and regulate various parameters associated with the respiration of a patient. As noted above, setup module 214 may receive manual settings as input from user interface 210, e.g., via a graphical user interface, or may receive preconfigured settings, from quick-start module 228 for example.

Setup module 214 may also include setup modules 216-226. Setup modules 216-226 may each be associated with a particular parameter for regulation and monitoring in a ventilatory system. Setup modules 216-226 are provided for exemplary purposes only and any number of useful setup modules representing any number of interesting and useful parameters may be provided. For example, in an embodiment, settings for frequency, f, may be accepted by a frequency module 216. Specifically, frequency may refer to a number of breaths over a period of time (e.g., breaths per minute) that should be delivered by the ventilator to the patient. Frequency module 216 may receive settings via manual clinician input or according to appropriate preconfigured settings based on a protocol. An appropriate frequency setting may be determined via any suitable means, for instance according to safety standards, clinical studies, or otherwise. Based on such standards and studies, appropriate protocol-specific settings may be uniformly determined for various subsets of a patient population, for example based on body weight, on gender and height, or on other ratio-metric patient data.

According to an embodiment, setup module 214 may also include a tidal volume module 218 for accepting parameter settings associated with tidal volume, $V_T$. Tidal volume refers to the total volume of air inhaled and exhaled for one respiratory cycle (e.g., in milliliters, mL). As such, the ventilator may be configured with tidal volume settings to ensure that the patient receives and exhales an adequate volume of air. Tidal volume module 218 may receive appropriate tidal volume settings via manual clinician input or according to appropriate preconfigured settings based on a protocol. As noted above, appropriate settings for tidal volume may be determined according to any suitable clinical evaluation or standard.

Setup module 214 may also include a flow module 220 for accepting parameter settings associated with flow. Flow refers to circuit airflow into and out of a patient's lungs and flow is governed by a pressure gradient between the lungs and the external atmospheric pressure. As such, a greater pressure gradient results in higher flow into or out of a patient's lungs. Very high flow may cause damage to a patient's lungs, trachea, etc., and an extremely low flow may indicate a leak or other unsafe condition. Thus, flow module 220 may accept settings for a maximum flow and a minimum flow, for example. As described above, flow module 220 may receive appropriate flow settings via manual clinician input or according to appropriate preconfigured settings, as determined according to any suitable clinical evaluation or standard.

According to embodiments, setup module 214 may also include a fractional inspired oxygen ($FiO_2$) module 222. $FiO_2$ refers to a percent of oxygen delivered to the patient, e.g., ranging from 21% (room air) to 100%. Standards may recommend an initial $FIO_2$ setting of 1.0 (100%) to allow the patient to get used to the ventilator without experiencing hypoxia (i.e., inadequate oxygen supply to the cells and tissues of the body). Again, $FiO_2$ module 222 may receive appropriate $FiO_2$ settings via manual clinician input or according to appropriate preconfigured settings, as determined according to any suitable clinical evaluation or standard.

Setup module 214 may also include a peak pressure module 224 for accepting settings for peak inspiratory pressure (i.e., PIP or ↑$P_{Peak}$). Peak inspiratory pressure refers to the highest pressure recorded at the end of inspiration (e.g., in cm $H_2O$). As pressures above certain levels may cause damage to the lungs, peak pressure module 224 may accept settings for a maximum pressure to be used by the ventilator to deliver respiration. Peak pressure module 224 may receive appropriate pressure settings via manual clinician input or according to appropriate preconfigured settings, as determined according to any suitable clinical evaluation or standard.

According to embodiments, setup module 214 may also include a positive end-expiratory pressure (PEEP) module 226. During each breath, air is delivered by the ventilator to the patient's lungs, which results in a net increase in pressure (e.g., in cm $H_2O$). In general, pressure is delivered from a baseline pressure, for example, atmospheric pressure is represented as a baseline pressure of zero cm $H_2O$. However, pressure may be delivered from a non-zero baseline pressure. Specifically, a baseline pressure above zero is referred to as positive end-expiratory pressure or PEEP. When the ventilator includes a PEEP setting, the patient is prevented from exhaling to zero cm $H_2O$, or atmospheric pressure. Thus, PEEP increases the volume of air left in the lungs at the end of expiration. As it relates to the present disclosure, PEEP module 226 may receive appropriate PEEP settings via manual clinician input or according to appropriate preconfigured settings, as determined according to any suitable clinical evaluation or standard.

Ventilator 202 may also include a quick-start module 228 in communication with setup module 214 and/or ventilation module 212. Quick-start module 228 may enable a clinician to efficiently and promptly initiate ventilation for a new patient by requiring only minimal setup input. For example, a main setup menu may provide a selection for initiating ventilation for a new patient or for a previous patient. When a new patient is selected for ventilation setup, a streamlined initiation process may be provided. For example, quick-start module 228 may provide an input element for "predicted weight," an input element for "gender and height," or any other suitable input element. Upon entering values into these input elements, a clinician may be presented with a plurality of appropriate parameter settings preconfigured for the patient according to an appropriate protocol or specification. Then, the clinician may simply select or otherwise activate a quick-start element, which serves to accept all of the appropriate preconfigured settings and to promptly initiate ventilation. Thereafter, parameter settings may be altered, or not, according to the needs of the patient as treatment progresses.

Specifically, quick-start module 228 may be in communication with a settings pre-configuration module 230. As mentioned above, many, if not all, of the initial settings for routine ventilatory parameters may be uniformly configured according to suitable clinical standards or specifications. Indeed, research may correlate these initial routine ventilatory settings with patient body weight, with patient gender and height, or with other patient-related ratio-metric variables. Institutions, such as clinics, hospitals, or other healthcare providers, may further develop institution-specific protocols by which initial ventilation setup is prescribed for all new patients, for example, based on body weight or gender and height, The present disclosure, via quick-start module 228 for example, enables institutions to pre-configure ventilators with initial parameter settings according to a suitable protocol or specification. Again, initial routine parameter settings may be developed according to clinical research or safety standards as deemed suitable by the institution. The above-mentioned setup modules 216-226 may then be populated with these protocol-specific parameter settings to provide appropriate default settings for use with the quick-start feature, e.g., based on body weight or gender and height.

Quick-start module 228 may further include a predicted weight module 232 and a gender and height module 234. Quick-start module 228 may also include other modules, for instance modules for receiving and processing a patient's gender and forearm length, or a patient's gender and distance from the patient's suprasternal notch to the umbilicus, or any other patient data suitable for correlation to protocol-specific settings (additional modules not shown) for which a nomogram has been developed and validated. For instance, via a calibrated bedside camera or other device, patient measurements for forearm length and/or a distance from the suprasternal notch to the umbilicus could be captured and correlated with protocol-specific settings. Indeed any patient data useful for correlation to protocol-specific settings may be measured, via a calibrated bedside camera or other device, and utilized within the spirit of the present disclosure.

According to some embodiments, initial parameter settings may be uniformly applied to new patients based on predicted body weight or gender and height. As such, appropriate parameter settings may be archived by the ventilator based on patient body weight or patient gender and height. Thereafter, when a clinician enters a predicted body weight as input, appropriate parameter settings may be accessed via predicted weight module 232, for example, and then presented to the clinician as pending default settings. When the clinician selects a quick-start element, for example, the pending default settings may be accepted and applied as actual ventilatory settings and ventilation may be promptly initiated for the new patient. In the alternative, when a clinician enters a patient's gender and height as input, appropriate parameter settings may be accessed via gender and height module 234, for example, and then presented to the clinician as pending default settings. When the clinician selects a quick-start element, the pending default settings may be accepted and applied as actual ventilatory settings and ventilation may be promptly initiated for the new patient.

As is clear from the above description, the quick-start feature provides numerous benefits. For example, an institution may ensure uniform initiation of ventilation based on institution-specific protocols. As routine parameter settings may be preconfigured, rather than repeatedly entered manually, consistency and uniformity of data input may be increased. Additionally, the quick-start feature promotes efficient and prompt initiation of ventilation for new patients. Again, rather than requiring clinicians to manually enter routine parameter settings for each new patient, reducing their attention to direct patient care, present embodiments provide a quick and accurate method for initiating new patient ventilation. These and many other benefits may be further described and illustrated herein.

Figure 3:
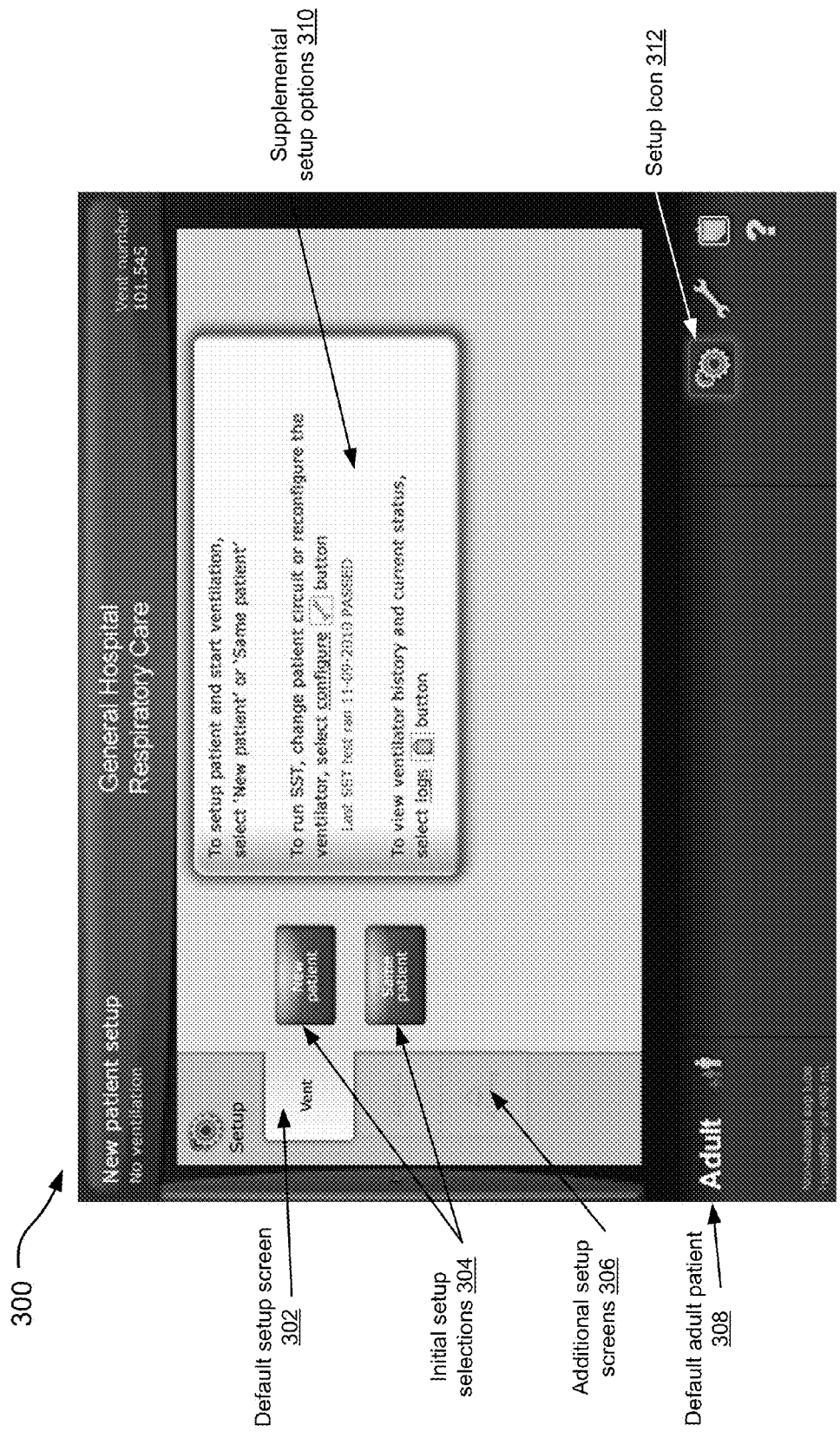
FIG. 3 is an illustration of an embodiment of a user interface for selecting a setup menu for a new patient.

FIG. 3 is an illustration of an embodiment of a user interface for selecting a setup menu for a new patient. Specifically, FIG. 3 illustrates an embodiment of a user interface displaying a New Patient Setup Interface 300.

New Patient Setup Interface 300 may be accessed via any suitable means, for example via a main ventilatory user interface on display module 204. As illustrated, New Patient Setup Interface 300 may provide one or more windows for display and one or more elements for selection and/or input. Windows may include the one or more elements, and additionally, may provide graphical displays, instructions, or other useful information to the clinician. Elements may be in the form of buttons, tabs, icons, input fields, etc., including any suitable element for input, selection, or control.

New Patient Setup Interface 300 may be identified by a title, or other identifying information, as illustrated in the upper left-hand corner of the displayed embodiment. In addition, a setup mode may be identified by a setup icon 312. Setup mode may be identified whenever a clinician accesses any of a number of setup screens, as described herein or otherwise available. In addition, New Patient Setup Interface 300 may include various default indicators, for example a default adult patient indicator 308. Note that patient setup may be configured for infants, children, adults, etc., and default adult patient indicator 308 may be accessed, via touching, clicking, or otherwise, and changed as necessary.

New Patient Setup Interface 300 may also be configured with a default setup screen 302. In the illustrated embodiment, the default setup screen 302 is labeled "vent" and is identified by a "vent tab." Setup screens may be identified and accessed via a tab, as illustrated, or any other access element, such as a button, icon, etc. In accordance with the present disclosure, there may be additional setup screens 306 that are unavailable upon initial access to the New Patient Setup Interface 300. As such, tabs or buttons for the additional setup screens 306, identified by an "apnea tab" and an "alarms tab"

in the illustration, may be grayed out or otherwise unavailable for selection upon initial access to New Patient Setup Interface 300.

Figure 4:
FIG. 4 is an illustration of an embodiment of a user interface for displaying and applying preconfigured ventilation modes and parameter settings during new patient setup.

Default setup screen 302, or the vent screen, may also provide supplemental setup options 310 to the clinician for selection. As illustrated, these supplemental setup options 310 may enable the clinician to access additional ventilatory screens that may provide other useful information to the clinician, such as test screens, history or status logs, etc. Further, default setup screen 302, may provide various elements for selection. For example, initial setup selections 304 may be displayed to a clinician. In the illustrated embodiment, initial setup selections 304 may include a "new patient" button, or other selection element, and a "same patient" button, or other selection element. Upon selection of the new patient button, a clinician may access a quick-start interface, as illustrated in FIG. 4. Note that the disclosed windows and elements, as described above with reference to FIG. 3 and below with reference to FIG. 4, are not to be understood as an exclusive array, as any number of similar suitable windows and elements may be displayed for the clinician within the spirit of the present disclosure. Further, the disclosed windows and elements are not to be understood as a necessary array, as any number of the disclosed windows and elements may be appropriately replaced by other suitable windows and elements without departing from the spirit of the present disclosure.

FIG. 4 is an illustration of an embodiment of a user interface for displaying and applying preconfigured ventilation modes and parameter settings during new patient setup. Specifically, FIG. 4 provides various windows and elements for quickly and promptly initiating ventilation for a new patient.

Upon selection of a new patient button, or other appropriate selection element, a Quick Start Interface 400 may be displayed to the clinician. As described above with reference to quick-start module 228, various preconfigured parameter settings may be useful for prompt initiation of ventilation for a new patient. These various preconfigured parameter settings may be correlated with a patient's body weight or a patient's gender and height. As such, Quick Start Interface 400 may provide input elements for entering a patient's predicted body weight, as illustrated by focused field 402, or for entering a patient's gender and height, as illustrated by non-focused fields 404. Additional input elements for entering a patient's gender and forearm length, or a patient's gender and a distance from the patient's suprasternal notch to the umbilicus, or any other patient data suitable for correlation to protocol-specific settings, may also be provided in embodiments of Quick Start Interface 400 (not shown).

Again, with reference to the discussion above, when a clinician enters a patient's predicted body weight, e.g., 50 kg, ventilatory parameter settings correlating to the entered body weight may be displayed to the clinician. According to the illustrated embodiment, the predicted body weight is shown as an italicized value in yellow font color. According to this embodiment, italicized, yellow data values represent pending parameters and settings. However, within the spirit of the present disclosure, pending values may be represented in any suitable form such that a clinician may quickly and easily recognize them as pending.

Further, according to the illustrated embodiment, upon entry of a predicted body weight, pending preconfigured modes 406 may be displayed to the clinician. Like preconfigured parameter settings discussed previously, preconfigured modes may be determined according to any suitable clinical study or standard and may further be incorporated into an institution-specific or other protocol. Pending preconfigured modes 406 may include default settings for initiating, for example, invasive ventilation rather than non-invasive ventilation (NIV). Additional default settings may indicate a type of ventilatory delivery, e.g., pressure controlled (PC) or volume controlled (VC), or a trigger type, e.g., pressure or flow. Indeed, suitable default modes may be preconfigured based on an applicable protocol, for instance, based on appropriate clinical research or otherwise. Default settings may be preconfigured for an initial quick-start setup, but may be later changed based on the needs and requirements of the patient during ventilatory treatment. As described above, pending preconfigured modes 406 may be displayed in yellow italics to indicate to the clinician a pending status.

Quick Start Interface 400 may also display pending preconfigured parameter settings 408. As with pending preconfigured modes 406, pending preconfigured parameter settings 408 may presented upon entry of a predicted body weight according to the illustrated embodiment. Pending preconfigured parameter settings 408 associated with the entered predicted body weight may include, inter alia, a frequency setting, a tidal volume setting, a maximum flow setting, an $FiO_2$ setting, and PIP and PEEP settings. As described above with reference to setup modules 216-226, these routine parameter settings may be preconfigured according to any suitable protocol, specification, or standard, for instance a clinic-specific, an institution-specific, or a physician-specific protocol. Further, the pending preconfigured parameter settings 408 may be displayed in yellow italics, or other form, to indicate that they are pending. Upon activation of quick-start element 410, the pending preconfigured parameter settings 408 may be accepted by the clinician, thereby becoming actual parameter settings, and ventilation may be promptly initiated.

According to alternative embodiments, pending default settings may be changed prior to initiating ventilation, via touching or clicking on an applicable parameter setting element of Quick Start Interface 400, for example. Note, however, that if default settings are changed, the quick-start feature may no longer be active and the clinician may be required to proceed with a fully or partially manual setup. Partial manual setup may allow the clinician to rely on some or most of the preconfigured ventilatory settings described above. In this case, pending preconfigured modes 406 or preconfigured parameter settings 408 may remain available for clinician acceptance even though some parameter settings were altered. Full manual setup, however, may clear all pending preconfigured settings upon a clinician change to one or more of the default settings. In this case, all parameter settings must be manually provided by the clinician via input fields in the user interface.

The previous discussion of Quick Start Interface 400 involved clinician entry of a patient's predicted body weight into focused field 402. However, the discussion above is equally applicable when the clinician enters a patient's gender and height, or any other suitable correlative patient data. Thereafter, as described above, pending preconfigured modes 406 and pending preconfigured parameter settings 408 may be displayed to the clinician upon entry of the patient's gender and height, or other patient data. Appropriate modes and parameter settings may be displayed based on previously determined correlations between patient gender and height, or other patient-related correlated variable, and the preconfigured modes and parameter settings. Indeed, any other patient data may be correlated to protocol-specific modes and parameter settings without departing from the spirit of the present disclosure.

It will be clear that the systems and methods described herein are well adapted to attain the ends and advantages mentioned as well as those inherent therein. Those skilled in the art will recognize that the methods and systems within this specification may be implemented in many manners and as such is not to be limited by the foregoing exemplified embodiments and examples. In other words, functional elements being performed by a single or multiple components, in various combinations of hardware and software, and individual functions can be distributed among software applications at either the client or server level. In this regard, any number of the features of the different embodiments described herein may be combined into one single embodiment and alternative embodiments having fewer than or more than all of the features herein described are possible.

While various embodiments have been described for purposes of this disclosure, various changes and modifications may be made which are well within the scope of the present invention. Numerous other changes may be made which will readily suggest themselves to those skilled in the art and which are encompassed in the spirit of the disclosure and as defined in the appended claims.

What is claimed is:

1. A ventilator comprising a display device for providing minimal-step ventilation setup for a new patient, the ventilator configured with a computer having a processor and a memory, the memory communicatively coupled to the processor and containing instructions that, when executed by the processor, cause the ventilator to provide a user interface, the user interface comprising:
at least one window associated with the user interface; and
one or more elements within the at least one window comprising:
at least one input element for receiving at least one patient variable selected from the group consisting of:
a patient predicted body weight and a patient gender and height; and
a selection element for initiating ventilation for the new patient according to a quick-start method, wherein the quick-start method initiates ventilation based on a plurality of preconfigured parameter settings comprising a preconfigured PEEP setting and a preconfigured ventilation trigger type, wherein the ventilator selects the plurality of preconfigured parameter settings based on the at least one patient variable.

2. The ventilator of claim 1, wherein the at least one input element comprises at least one of:
an input element for inputting patient predicted body weight;
one or more input elements for inputting patient gender and height;
one or more input elements for inputting a patient gender and forearm length; and
one or more input elements for inputting a patient gender and a distance from a patient suprasternal notch to a patient umbilicus.

3. The ventilator of claim 1, wherein at least one preconfigured ventilation mode is displayed upon receiving the at least one patient variable, and wherein the at least one preconfigured ventilation mode is determined to be appropriate for the at least one patient variable by a protocol.

4. The ventilator of claim 3, wherein a selection is received for initiating ventilation according to the quick-start method, and wherein ventilation is initiated based on the at least one preconfigured ventilation mode displayed.

5. The ventilator of claim 3, wherein the at least one preconfigured ventilation mode is displayed in a form indicating that it is pending.

6. The ventilator of claim 1, wherein the plurality of preconfigured parameter settings are displayed upon receiving the at least one patient variable, and wherein the plurality of preconfigured parameter settings are determined to be appropriate for the at least one patient variable by a protocol.

7. The ventilator of claim 6, wherein a selection is received for initiating ventilation according to the quick-start method, and wherein ventilation is initiated based on the plurality of preconfigured parameter settings displayed.

8. The ventilator of claim 6, wherein the plurality of preconfigured parameter settings are displayed in a form indicating that they are pending.

9. A non-transitory computer-readable storage medium having instructions that when executed provide a user interface for providing minimal-step ventilation setup for a new patient, the user interface comprising:
at least one window associated with the user interface; and
one or more elements within the at least one window comprising:
at least one input element for receiving at least one patient variable selected from the group consisting of:
a patient predicted body weight and a patient gender and height; and
a selection element for initiating ventilation for the new patient according to a quick-start method, wherein the quick-start method initiates ventilation based on a plurality of preconfigured parameter settings comprising at least a preconfigured ventilation trigger type, wherein the ventilator selects the plurality of preconfigured parameter settings based on the at least one patient variable.

10. The non-transitory computer-readable storage medium of claim 9, wherein the at least one input element comprises at least one of:
an input element for inputting patient predicted body weight;
one or more input elements for inputting patient gender and height;
one or more input elements for inputting a patient gender and forearm length; and
one or more input elements for inputting a patient gender and a distance from a patient suprasternal notch to a patient umbilicus.

11. The non-transitory computer-readable storage medium of claim 9, wherein at least one preconfigured ventilation mode is displayed upon receiving the at least one patient variable, and wherein the at least one preconfigured ventilation mode is determined to be appropriate for the at least one patient variable by a protocol.

12. The non-transitory computer-readable storage medium of claim 11, wherein a selection is received for initiating ventilation according to the quick-start method, and wherein ventilation is initiated based on the at least one preconfigured ventilation mode displayed.

13. The non-transitory computer-readable storage medium of claim 9, wherein the plurality of preconfigured parameter settings are displayed upon receiving the at least one patient variable, and wherein the plurality of preconfigured parameter settings are determined to be appropriate for the at least one patient variable by a protocol.

14. The non-transitory computer-readable storage medium of claim 13, wherein a selection is received for initiating ventilation according to the quick-start method, and wherein ventilation is initiated based on the plurality of preconfigured parameter settings displayed.

15. The non-transitory computer-readable storage medium of claim 9, wherein the non-transitory computer-readable storage medium is selected from a group consisting of: RAM, ROM, EPROM, EEPROM, flash memory, solid state memory technology, CD-ROM, DVD, optical storage, magnetic cassettes, magnetic tape, magnetic disk storage, and magnetic storage devices.

16. A ventilatory system for providing a user interface for providing minimal-step ventilation setup for a new patient, comprising:
   at least one window associated with the user interface; and
   one or more elements within the at least one window comprising:
      at least one input element for receiving at least one patient variable selected from the group consisting of: a patient predicted body weight and a patient gender and height; and
      a selection element for initiating ventilation for the new patient according to a quick-start method, wherein the quick-start method initiates ventilation based on a plurality of preconfigured parameter settings comprising at least a preconfigured PEEP setting, wherein the ventilator selects the plurality of preconfigured parameter settings based on the at least one patient variable.

17. The ventilatory system of claim 16, wherein the at least one input element comprise at least one of:
   an input element for inputting patient predicted body weight;
   one or more input elements for inputting patient gender and height;
   one or more input elements for inputting a patient gender and forearm length; and
   one or more input elements for inputting a patient gender and a distance from a patient suprasternal notch to a patient umbilicus.

18. The ventilatory system of claim 16, wherein at least one preconfigured ventilation mode is displayed upon receiving the at least one patient variable, and wherein the at least one preconfigured ventilation mode is determined to be appropriate for the at least one patient variable by a protocol.

19. The ventilatory system of claim 16, wherein the plurality of preconfigured parameter settings are displayed upon receiving the at least one patient variable, and wherein the plurality of preconfigured parameter settings are determined to be appropriate for the at least one patient variable by a protocol.

20. The ventilatory system of claim 19, wherein a selection is received for initiating ventilation according to the quick-start method, and wherein ventilation is initiated based on the plurality of preconfigured parameter settings displayed.

* * * * *